United States Patent
Klaenhammer et al.

(10) Patent No.: US 9,040,302 B2
(45) Date of Patent: May 26, 2015

(54) GENETICALLY MODIFIED STREPTOCOCCUS THERMOPHILUS BACTERIUM

(75) Inventors: Todd R. Klaenhammer, Raleigh, NC (US); Richard L. Guerrant, Charlottesville, VA (US); Glynis L. Kolling, Scottsville, VA (US); Evelyn Durmaz, Cary, NC (US); Michael P. Timko, Charlottesville, VA (US); Cirle Alcantara Warren, Waynesboro, VA (US)

(73) Assignees: North Carolina State University, Raleigh, NC (US); University of Virginia Patent Foundation, Charlottesvile, VA (US)

( * ) Notice: Subject to any disclaimer, the term of this patent is extended or adjusted under 35 U.S.C. 154(b) by 0 days.

(21) Appl. No.: 13/697,860

(22) PCT Filed: May 19, 2011

(86) PCT No.: PCT/US2011/037149
§ 371 (c)(1),
(2), (4) Date: Jan. 25, 2013

(87) PCT Pub. No.: WO2011/146715
PCT Pub. Date: Nov. 24, 2011

(65) Prior Publication Data
US 2013/0259834 A1  Oct. 3, 2013

Related U.S. Application Data

(60) Provisional application No. 61/346,107, filed on May 19, 2010, provisional application No. 61/436,452, filed on Jan. 26, 2011.

(51) Int. Cl.
| | | |
|---|---|---|
| *A61K 35/74* | (2006.01) | |
| *A61K 38/16* | (2006.01) | |
| *A23C 9/123* | (2006.01) | |
| *A23L 1/30* | (2006.01) | |
| *C12N 1/06* | (2006.01) | |
| *C12P 21/02* | (2006.01) | |
| *A61K 35/00* | (2006.01) | |

(52) U.S. Cl.
CPC ............. *A61K 38/164* (2013.01); *A23C 9/1238* (2013.01); *A23L 1/3014* (2013.01); *A61K 2035/11* (2013.01); *C12N 1/06* (2013.01); *C12P 21/02* (2013.01); *A61K 35/74* (2013.01)

(58) Field of Classification Search
CPC .................. A23V 2002/00; A23V 2200/3204; C07K 14/315; C07K 2317/14; C07K 2317/76; C07K 2317/31; C07K 14/195; A61K 38/00; A61K 48/00; A61K 39/092; A61K 2039/6006; A61K 45/06; A61K 2039/505; A61K 2300/00; C12P 13/06; C12P 13/14
See application file for complete search history.

(56) References Cited

U.S. PATENT DOCUMENTS 6,649,746 B1 * 11/2003 Timko et al. ................. 536/23.5
2007/0276124 A1 * 11/2007 Turner et al. .................. 530/324

FOREIGN PATENT DOCUMENTS

| EP | 1 177 794 A2 | 2/2002 |
| EP | 2248823 A1 * | 11/2010 |
| WO | WO 00/68251 A1 | 11/2000 |
| WO | WO 2005/040200 A1 | 5/2005 |

OTHER PUBLICATIONS

Somkuti et al., "Permeabilization of *Streptococcus thermophilus* and the expression of beta-galactosidase." Enzyme Microb. Technol. (Jul. 1994); 16(7): pp. 573-576.*
Chen, X., et al., "A Mouse Model of *Clostridium difficile*—Associated Disease," *Gastroenterology*, 2008, vol. 135(6), pp. 1984-1992.
Somkuti, G., et al., "Permeabilization of *Streptococcus thermophilus* and the expression of beta-galactosidase," *Enzyme Microb. Technol.*, 1994, vol. 16(7), pp. 573-576.

* cited by examiner

*Primary Examiner* — Thaian N Ton
*Assistant Examiner* — Titilayo Moloye
(74) *Attorney, Agent, or Firm* — Alston & Bird LLP

(57) ABSTRACT

Methods and compositions for targeted delivery of biotherapeutics are provided. The compositions comprise bile-sensitive *St. thermophilus* bacteria modified to release a biotherapeutic agent following bile exposure. Biotherapeutic agents released by the *St. thermophilus* bacteria disclosed herein include AQ and AQR rich peptides. Methods of the invention comprise administering to a subject a *St. thermophilus* bacterium modified to release a biotherapeutic agent following bile exposure. Administration of the *St. thermophilus* bacterium promotes a desired therapeutic response. The bacterium may be modified to express and release AQ or AQR rich peptides which subsequently inhibit cellular apoptosis or reduce mucosal damage. Thus, methods of the invention find use in treating or preventing a variety of gastrointestinal disorders including *C. difficile* infection and antibiotic-associated diarrhea.

8 Claims, 8 Drawing Sheets

SEQUENCE LISTING

```
<160> NUMBER OF SEQ ID NOS: 18

<210> SEQ ID NO 1
<211> LENGTH: 222
<212> TYPE: DNA
<213> ORGANISM: Artificial Sequence
<220> FEATURE:
<223> OTHER INFORMATION: AGRP-FH0
<220> FEATURE:
<221> NAME/KEY: CDS
<222> LOCATION: (1)...(222)

<400> SEQUENCE: 1 cgg gcc atg gat tat aaa gac gac gat gat aaa gcg ctg cag caa gct      48
Arg Ala Met Asp Tyr Lys Asp Asp Asp Asp Lys Ala Leu Gln Gln Ala
 1               5                  10                  15 cag cag gct cag cag aaa gtt cag cag gat atc cag cag ccg gcg caa      96
Gln Gln Ala Gln Gln Lys Val Gln Gln Asp Ile Gln Gln Pro Ala Gln
            20                  25                  30 cag gcc cag cag ggt cag cag gtt cag cag gcc caa cag gac att cag     144
Gln Ala Gln Gln Gly Gln Gln Val Gln Gln Ala Gln Gln Asp Ile Gln
        35                  40                  45
```

| | |
|---|---|
| cag aca gca cag caa gca cag cag att cag cag cgt cag cag aaa tat<br>Gln Thr Ala Gln Gln Ala Gln Gln Ile Gln Gln Arg Gln Gln Lys Tyr<br>    50                  55                  60 | 192 |
| ccg tat gat gtg ccg gac tat gct cta gac<br>Pro Tyr Asp Val Pro Asp Tyr Ala Leu Asp<br>65                  70 | 222 |

<210> SEQ ID NO 2
<211> LENGTH: 74
<212> TYPE: PRT
<213> ORGANISM: Artificial Sequence
<220> FEATURE:
<223> OTHER INFORMATION: AGRP-FH0

<400> SEQUENCE: 2

Arg Ala Met Asp Tyr Lys Asp Asp Asp Lys Ala Leu Gln Gln Ala
1               5                   10                  15

Gln Gln Ala Gln Gln Lys Val Gln Gln Asp Ile Gln Gln Pro Ala Gln
            20                  25                  30

Gln Ala Gln Gln Gly Gln Gln Val Gln Gln Ala Gln Gln Asp Ile Gln
        35                  40                  45

Gln Thr Ala Gln Gln Ala Gln Gln Ile Gln Gln Arg Gln Gln Lys Tyr
    50                  55                  60

Pro Tyr Asp Val Pro Asp Tyr Ala Leu Asp
65                  70

<210> SEQ ID NO 3
<211> LENGTH: 270
<212> TYPE: DNA
<213> ORGANISM: Artificial Sequence
<220> FEATURE:
<223> OTHER INFORMATION: AGRP-FH1
<220> FEATURE:
<221> NAME/KEY: CDS
<222> LOCATION: (1)...(270)

<400> SEQUENCE: 3

| | |
|---|---|
| cgg gcc atg gat tat aaa gat gat gat gat aaa gcc cag gca cag cag<br>Arg Ala Met Asp Tyr Lys Asp Asp Asp Asp Lys Ala Gln Ala Gln Gln<br>1               5                   10                  15 | 48 |
| ggt caa cgt cag gca caa cag atc cag caa gca cag cag ggc cag cgc<br>Gly Gln Arg Gln Ala Gln Gln Ile Gln Gln Ala Gln Gln Gly Gln Arg<br>            20                  25                  30 | 96 |
| cag cag gcg cag gcc caa cag ggt cag cgc caa gct cag caa att caa<br>Gln Gln Ala Gln Ala Gln Gln Gly Gln Arg Gln Ala Gln Gln Ile Gln<br>        35                  40                  45 | 144 |
| cag gct cag cag gga cag cgt cag cag gct cag gcc cag cag ggt cag<br>Gln Ala Gln Gln Gly Gln Arg Gln Gln Ala Gln Ala Gln Gln Gly Gln<br>    50                  55                  60 | 192 |
| cag gcc cag cag att cag cag gcg cag caa ggt cag cgt cag cag tat<br>Gln Ala Gln Gln Ile Gln Gln Ala Gln Gln Gly Gln Arg Gln Gln Tyr<br>65                  70                  75                  80 | 240 |
| ccg tac gac gtt ccg gac tac gct cta gac<br>Pro Tyr Asp Val Pro Asp Tyr Ala Leu Asp<br>            85                  90 | 270 |

<210> SEQ ID NO 4
<211> LENGTH: 90
<212> TYPE: PRT
<213> ORGANISM: Artificial Sequence
<220> FEATURE:
<223> OTHER INFORMATION: AGRP-FH1

<400> SEQUENCE: 4

Arg Ala Met Asp Tyr Lys Asp Asp Asp Lys Ala Gln Ala Gln Gln
1               5                   10                  15

Gly Gln Arg Gln Ala Gln Gln Ile Gln Gln Ala Gln Gln Gly Gln Arg
            20                  25                  30

Gln Gln Ala Gln Ala Gln Gln Gly Gln Arg Gln Ala Gln Gln Ile Gln
        35                  40                  45

Gln Ala Gln Gln Gly Gln Arg Gln Gln Ala Gln Ala Gln Gln Gly Gln
50                  55                  60

Gln Ala Gln Gln Ile Gln Gln Ala Gln Gln Gly Gln Arg Gln Gln Tyr
65                  70                  75                  80

Pro Tyr Asp Val Pro Asp Tyr Ala Leu Asp
                85                  90

<210> SEQ ID NO 5
<211> LENGTH: 318
<212> TYPE: DNA
<213> ORGANISM: Artificial Sequence
<220> FEATURE:
<223> OTHER INFORMATION: AGRP-FH2
<220> FEATURE:
<221> NAME/KEY: CDS
<222> LOCATION: (1)...(318)

<400> SEQUENCE: 5 cgg gcc atg gat tac aaa gat gat gat gat aaa gcc cag gcc cag caa        48
Arg Ala Met Asp Tyr Lys Asp Asp Asp Asp Lys Ala Gln Ala Gln Gln
1               5                   10                  15 cgt ggt cag gca cag cag cgt ggg cag atc cag cag cgc ggc cag cgc        96
Arg Gly Gln Ala Gln Gln Arg Gly Gln Ile Gln Gln Arg Gly Gln Arg
            20                  25                  30 gca cag gcg cag caa cgc ggc cag gcc cag cag cgt ggc caa atc cag       144
Ala Gln Ala Gln Gln Arg Gly Gln Ala Gln Gln Arg Gly Gln Ile Gln
        35                  40                  45 cag cgt ggt cag cgc gcc cag gct cag caa cgc gga cag gct caa caa       192
Gln Arg Gly Gln Arg Ala Gln Ala Gln Gln Arg Gln Ala Gln Gln
50                  55                  60 cgt ggt cag att caa cag cgc ggg cag cgc gcg caa gcc caa caa cgc       240
Arg Gly Gln Ile Gln Gln Arg Gly Gln Arg Ala Gln Ala Gln Gln Arg
65                  70                  75                  80 ggt cag gcg cag cag cgc ggt cag att cag cag cgt gga caa cgc tat       288
Gly Gln Ala Gln Gln Arg Gly Gln Ile Gln Gln Arg Gly Gln Arg Tyr
                85                  90                  95 cct tat gat gtc cct gat tac gct cta gac                               318
Pro Tyr Asp Val Pro Asp Tyr Ala Leu Asp
                100                 105

<210> SEQ ID NO 6
<211> LENGTH: 106
<212> TYPE: PRT
<213> ORGANISM: Artificial Sequence
<220> FEATURE:
<223> OTHER INFORMATION: AGRP-FH2

<400> SEQUENCE: 6

Arg Ala Met Asp Tyr Lys Asp Asp Asp Lys Ala Gln Ala Gln Gln
1               5                   10                  15

Arg Gly Gln Ala Gln Gln Arg Gly Gln Ile Gln Gln Arg Gly Gln Arg
            20                  25                  30

Ala Gln Ala Gln Gln Arg Gly Gln Ala Gln Gln Arg Gly Gln Ile Gln
        35                  40                  45

```
Gln Arg Gly Gln Arg Ala Gln Ala Gln Gln Arg Gly Gln Ala Gln Gln
        50                  55                  60
Arg Gly Gln Ile Gln Gln Arg Gly Gln Arg Ala Gln Ala Gln Gln Arg
 65                  70                  75                  80
Gly Gln Ala Gln Gln Arg Gly Gln Ile Gln Gln Arg Gly Gln Arg Tyr
                 85                  90                  95
Pro Tyr Asp Val Pro Asp Tyr Ala Leu Asp
            100                 105
```

```
<210> SEQ ID NO 7
<211> LENGTH: 247
<212> TYPE: DNA
<213> ORGANISM: Artificial Sequence
<220> FEATURE:
<223> OTHER INFORMATION: AGRP-FH0s
<220> FEATURE:
<221> NAME/KEY: CDS
<222> LOCATION: (26)...(247)

<400> SEQUENCE: 7
ctagaatatt tcaggcccgg tgtcc atg gcc cgg gcc atg gat tat aaa gac      52
                            Met Ala Arg Ala Met Asp Tyr Lys Asp
                              1               5 gac gat gat aaa gcg ctg cag caa gct cag cag gct cag cag aaa gtt    100
Asp Asp Asp Lys Ala Leu Gln Gln Ala Gln Gln Ala Gln Gln Lys Val
 10                  15                  20                  25 cag cag gat atc cag cag ccg gcg caa cag gcc cag cag ggt cag cag    148
Gln Gln Asp Ile Gln Gln Pro Ala Gln Gln Ala Gln Gln Gly Gln Gln
                 30                  35                  40 gtt cag cag gcc caa cag gac att cag cag aca gca cag caa gca cag    196
Val Gln Gln Ala Gln Gln Asp Ile Gln Gln Thr Ala Gln Gln Ala Gln
             45                  50                  55 cag att cag cag cgt cag cag aaa tat ccg tat gat gtg ccg gac tat    244
Gln Ile Gln Gln Arg Gln Gln Lys Tyr Pro Tyr Asp Val Pro Asp Tyr
         60                  65                  70 gct                                                                247
Ala

<210> SEQ ID NO 8
<211> LENGTH: 74
<212> TYPE: PRT
<213> ORGANISM: Artificial Sequence
<220> FEATURE:
<223> OTHER INFORMATION: AGRP-FH0s

<400> SEQUENCE: 8

Met Ala Arg Ala Met Asp Tyr Lys Asp Asp Asp Asp Lys Ala Leu Gln
  1               5                  10                  15
Gln Ala Gln Gln Ala Gln Gln Lys Val Gln Gln Asp Ile Gln Gln Pro
                 20                  25                  30
Ala Gln Gln Ala Gln Gln Gly Gln Gln Val Gln Gln Ala Gln Gln Asp
             35                  40                  45
Ile Gln Gln Thr Ala Gln Gln Ala Gln Gln Ile Gln Gln Arg Gln Gln
         50                  55                  60
Lys Tyr Pro Tyr Asp Val Pro Asp Tyr Ala
 65                  70

<210> SEQ ID NO 9
<211> LENGTH: 295
<212> TYPE: DNA
<213> ORGANISM: Artificial Sequence
```

<220> FEATURE:
<223> OTHER INFORMATION: AGRP-FH1
<220> FEATURE:
<221> NAME/KEY: CDS
<222> LOCATION: (32)...(295)

<400> SEQUENCE: 9

```
ctagaatatt tcaggcccgg tgtccatggc c cgg gcc atg gat tat aaa gat         52
                                   Arg Ala Met Asp Tyr Lys Asp
                                    1               5 gat gat gat aaa gcc cag gca cag cag ggt caa cgt cag gca caa cag       100
Asp Asp Asp Lys Ala Gln Ala Gln Gln Gly Gln Arg Gln Ala Gln Gln
         10                  15                  20 atc cag caa gca cag cag ggc cag cgc cag cag gcg cag gcc caa cag       148
Ile Gln Gln Ala Gln Gln Gly Gln Arg Gln Gln Ala Gln Ala Gln Gln
     25                  30                  35 ggt cag cgc caa gct cag caa att caa cag gct cag cag gga cag cgt       196
Gly Gln Arg Gln Ala Gln Gln Ile Gln Gln Ala Gln Gln Gly Gln Arg
 40                  45                  50                  55 cag cag gct cag gcc cag cag ggt cag cag gcc cag cag att cag cag       244
Gln Gln Ala Gln Ala Gln Gln Gly Gln Gln Ala Gln Gln Ile Gln Gln
                 60                  65                  70 gcg cag caa ggt cag cgt cag cag tat ccg tac gac gtt ccg gac tac       292
Ala Gln Gln Gly Gln Arg Gln Gln Tyr Pro Tyr Asp Val Pro Asp Tyr
         75                  80                  85 gct                                                                   295
Ala
```

<210> SEQ ID NO 10
<211> LENGTH: 88
<212> TYPE: PRT
<213> ORGANISM: Artificial Sequence
<220> FEATURE:
<223> OTHER INFORMATION: AGRP-FH1

<400> SEQUENCE: 10

```
Arg Ala Met Asp Tyr Lys Asp Asp Asp Lys Ala Gln Ala Gln Gln
 1               5                  10                  15

Gly Gln Arg Gln Ala Gln Gln Ile Gln Gln Ala Gln Gln Gly Gln Arg
             20                  25                  30

Gln Gln Ala Gln Ala Gln Gln Gly Gln Arg Gln Ala Gln Gln Ile Gln
         35                  40                  45

Gln Ala Gln Gln Gly Gln Arg Gln Gln Ala Gln Ala Gln Gln Gly Gln
     50                  55                  60

Gln Ala Gln Gln Ile Gln Gln Ala Gln Gln Gly Gln Arg Gln Gln Tyr
 65                  70                  75                  80

Pro Tyr Asp Val Pro Asp Tyr Ala
                 85
```

<210> SEQ ID NO 11
<211> LENGTH: 343
<212> TYPE: DNA
<213> ORGANISM: Artificial Sequence
<220> FEATURE:
<223> OTHER INFORMATION: AGRP-FH2
<220> FEATURE:
<221> NAME/KEY: CDS
<222> LOCATION: (32)...(343)

<400> SEQUENCE: 11

```
ctagaatatt tcaggcccgg tgtccatggc c cgg gcc atg gat tac aaa gat        52
                                   Arg Ala Met Asp Tyr Lys Asp
                                     1               5 gat gat gat aaa gcc cag gcc cag caa cgt ggt cag gca cag cag cgt      100
Asp Asp Asp Lys Ala Gln Ala Gln Gln Arg Gly Gln Ala Gln Gln Arg
         10                  15                  20 ggg cag atc cag cag cgc ggc cag cgc gca cag gcg cag caa cgc ggc      148
Gly Gln Ile Gln Gln Arg Gly Gln Arg Ala Gln Ala Gln Gln Arg Gly
     25                  30                  35 cag gcc cag cag cgt ggc caa atc cag cag cgt ggt cag cgc gcc cag      196
Gln Ala Gln Gln Arg Gly Gln Ile Gln Gln Arg Gly Gln Arg Ala Gln
 40                  45                  50                  55 gct cag caa cgc gga cag gct caa caa cgt ggt cag att caa cag cgc      244
Ala Gln Gln Arg Gly Gln Ala Gln Gln Arg Gly Gln Ile Gln Gln Arg
                 60                  65                  70 ggg cag cgc gcg caa gcc caa caa cgc ggt cag gcg cag cag cgc ggt      292
Gly Gln Arg Ala Gln Ala Gln Gln Arg Gly Gln Ala Gln Gln Arg Gly
             75                  80                  85 cag att cag cag cgt gga caa cgc tat cct tat gat gtc cct gat tac      340
Gln Ile Gln Gln Arg Gly Gln Arg Tyr Pro Tyr Asp Val Pro Asp Tyr
         90                  95                 100 gct                                                                  343
Ala
```

<210> SEQ ID NO 12
<211> LENGTH: 104
<212> TYPE: PRT
<213> ORGANISM: Artificial Sequence
<220> FEATURE:
<223> OTHER INFORMATION: AGRP-FH2

<400> SEQUENCE: 12

```
Arg Ala Met Asp Tyr Lys Asp Asp Asp Lys Ala Gln Ala Gln Gln
  1               5                  10                  15

Arg Gly Gln Ala Gln Gln Arg Gly Gln Ile Gln Gln Arg Gly Gln Arg
             20                  25                  30

Ala Gln Ala Gln Gln Arg Gly Gln Ala Gln Gln Arg Gly Gln Ile Gln
         35                  40                  45

Gln Arg Gly Gln Arg Ala Gln Ala Gln Gln Arg Gly Gln Ala Gln Gln
     50                  55                  60

Arg Gly Gln Ile Gln Gln Arg Gly Gln Arg Ala Gln Ala Gln Gln Arg
 65                  70                  75                  80

Gly Gln Ala Gln Gln Arg Gly Gln Ile Gln Gln Arg Gly Gln Arg Tyr
                 85                  90                  95

Pro Tyr Asp Val Pro Asp Tyr Ala
            100
```

<210> SEQ ID NO 13
<211> LENGTH: 8
<212> TYPE: PRT
<213> ORGANISM: Artificial Sequence
<220> FEATURE:
<223> OTHER INFORMATION: FLAG-epitope

<400> SEQUENCE: 13

```
Asp Tyr Lys Asp Asp Asp Asp Lys
  1               5
```

```
<210> SEQ ID NO 14
<211> LENGTH: 20
<212> TYPE: DNA
<213> ORGANISM: Artificial Sequence
<220> FEATURE:
<223> OTHER INFORMATION: SauI Forward Primer
<220> FEATURE:
<221> NAME/KEY: misc_feature
<222> LOCATION: (1)...(20)

<400> SEQUENCE: 14
tgctgaagag catctgattg                                              20

<210> SEQ ID NO 15
<211> LENGTH: 22
<212> TYPE: DNA
<213> ORGANISM: Artificial Sequence
<220> FEATURE:
<223> OTHER INFORMATION: AGRP-FH0 internal primer
<220> FEATURE:
<221> NAME/KEY: misc_feature
<222> LOCATION: (1)...(22)

<400> SEQUENCE: 15
ggccatggat tataaagacg ac                                           22

<210> SEQ ID NO 16
<211> LENGTH: 22
<212> TYPE: DNA
<213> ORGANISM: Artificial Sequence
<220> FEATURE:
<223> OTHER INFORMATION: AGRP-FH1 internal primer
<220> FEATURE:
<221> NAME/KEY: misc_feature
<222> LOCATION: (1)...(22)

<400> SEQUENCE: 16
gggtcaacgt caggcacaac ag                                           22

<210> SEQ ID NO 17
<211> LENGTH: 22
<212> TYPE: DNA
<213> ORGANISM: Artificial Sequence
<220> FEATURE:
<223> OTHER INFORMATION: AGRP-FH2 internal primer
<220> FEATURE:
<221> NAME/KEY: misc_feature
<222> LOCATION: (1)...(22)

<400> SEQUENCE: 17
gataaagccc aggcccagca ac                                           22

<210> SEQ ID NO 18
<211> LENGTH: 20
<212> TYPE: DNA
<213> ORGANISM: Artificial Sequence
<220> FEATURE:
<223> OTHER INFORMATION: SauI Reverse Primer
<220> FEATURE:
<221> NAME/KEY: misc_feature
<222> LOCATION: (1)...(20)

<400> SEQUENCE: 18
cccgttagtt gaagaaggtt                                              20
```

US 9,040,302 B2

GENETICALLY MODIFIED STREPTOCOCCUS THERMOPHILUS BACTERIUM

CROSS-REFERENCE TO RELATED APPLICATIONS

This application is the U.S. National Stage of International Application PCT/US2011/037149 filed May 19, 2011, which designates the U.S and was published by the International Bureau in English on Nov. 24, 2011, and which claims the benefit of U.S. Provisional Application Nos. 61/346,107, filed May 19, 2010, and 61/436,452, filed Jan. 26, 2011, all of which are hereby incorporated by reference in their entirety.

FEDERALLY SPONSORED RESEARCH OR DEVELOPMENT

This invention was made with United States Government support under U54 AI57168 awarded by NIH-MARCE and U01 AI075526 awarded by NIH. The United States Government has certain rights in the invention.

FIELD OF THE INVENTION

The present invention relates to methods and compositions for targeted delivery of biotherapeutic agents.

REFERENCE TO ELECTRONICALLY-SUBMITTED SEQUENCE LISTING

The official copy of the sequence listing is submitted electronically via EFS-Web as an ASCII formatted sequence listing with a file named 405777SEQLIST.txt, created on May 19, 2011, and having a size of 15 KB and is filed concurrently with the specification. The sequence listing contained in this ASCII formatted document is part of the specification and is herein incorporated by reference in its entirety.

BACKGROUND OF THE INVENTION

Lactic acid bacteria (LAB) have been consumed safely by humans in various fermented food and dairy products. Many of these LAB hold a "Generally Recognized as Safe" (GRAS) status and can be consumed at levels approaching 1 trillion cells per gram of food, without adverse effects. Selected members of the LAB are acid tolerant, but bile sensitive, and do not survive passage through the gastrointestinal tract. Thus, bile exposure of selected LAB can result in disruption of cellular integrity, permeabilization, and release of intracellular proteins. Such microbes can be orally delivered through the stomach to the small intestine for targeted delivery of biotherapeutic peptides upon permeabilization of the microbe by bile. In addition, the microbe dies upon bile permeabilization and would, therefore, remain contained within the GI tract following oral delivery.

*Streptococcus thermophilus*, is a gram-positive lactic acid bacterium of the viridans group. *St. thermophilus* is commonly found in fermented milk products including yogurt, fermented milk, and cheese. Commercial dairy products comprising *St. thermophilus* can be used as a treatment for antibiotic-associated diarrhea (Hickson, 2007, 335(7610):80).

*Clostridium difficile* (*C. difficile*) is the most common cause of nosocomial bacterial diarrhea and accounts for 10-20% of the cases of antibiotic-associated diarrhea. *C. difficile* infection can result in asymptomatic carriage, mild diarrhea, or fulminant pseudomembranous colitis. This anaerobic bacterium causes intestinal damage primarily through the actions of two large exotoxins, toxin A and toxin B. Purified toxin A (TxA) causes intestinal secretion, destruction of the intestinal epithelium and hemorrhagic colitis when introduced in vivo to the intestinal lumen. The mechanism of TxA-induced enteritis involves toxin binding to enterocyte receptors, leading to activation of sensory and enteric nerves that results in enhanced intestinal secretion and motility, degranulation of mast cells, and infiltration of the mucosa by neutrophils. In addition to its proinflammatory and prosecretory activities, TxA induces apoptosis and nonapoptotic cell death, which could contribute to intestinal mucosal disruption. Specifically, TxA has been shown to affect important aspects of the intestinal mucosal repair process such as epithelial cell migration, apoptosis, and the development of transepithelial resistance (Brito et al. (2005) Dig Dis and Sci 50(7): 1271-1278).

Glutamine (Gln) is the primary fuel for both enterocyte and the colonocyte and is necessary for the maintenance of intestinal structure in both normal and stressed states (Cario et al., Eur J Clin Invest. 2000 May 30(5):419429). Studies have shown glutamine supplementation to prevent villous atrophy, and bacterial translocation, conditions associated with standard parenteral nutrition (Van Der Hulst et al., Lancet 1993 341:1363). Glutamine plays a pivotal role in several metabolic pathways. Its importance in tissue culture has long been recognized, and it is a key nitrogen donor for the biosynthesis of nucleotides, amino sugars, and amino acids in mammalian cells. It is anticipated that the availability of glutamine will be especially important during persistent diarrhea and malnutrition, when the mucosal barrier function is often disrupted. Animal studies have shown that glutamine-enriched nutrition can attenuate bacterial translocation, improve nutritional status, decrease intestinal injury and result in improved survival in a lethal model of methotrexate-induced enterocolitis.

Alanyl-glutamine (Ala-Gin) is a stable glutamine derivative that has been shown to be much more stable in acidic water solutions (such as they would be expected to face in a patient's stomach or intestine) and to drive salt and water absorption comparable to, if not better, than glucose (see U.S. Pat. No. 5,561,111, the disclosure of which is expressly incorporated herein). Stable glutamine derivatives are useful not only in malnourished children with diarrhea, but also in patients kept too long on parenteral (IV) fluids or tube feedings or in those with damaged intestinal mucosa from infection or chemotherapy.

BRIEF SUMMARY OF THE INVENTION

Methods and compositions for targeted delivery of biotherapeutics are provided. The compositions comprise bile-sensitive *St. thermophilus* bacteria modified to release a biotherapeutic agent following bile exposure. Biotherapeutic agents released by the *St. thermophilus* bacteria disclosed herein include AQ and AQR rich peptides. Methods of the invention comprise administering to a subject a *St. thermophilus* bacterium modified to release a biotherapeutic agent following bile exposure. Administration of the *St. thermophilus* bacterium promotes a desired therapeutic response. The bacterium may be modified to express and release AQ or AQR rich peptides which subsequently inhibit cellular apoptosis or reduce mucosal damage. Thus, methods of the invention find use in treating or preventing a variety of gastrointestinal disorders including *C. difficile* infection and antibiotic-associated diarrhea.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 5:
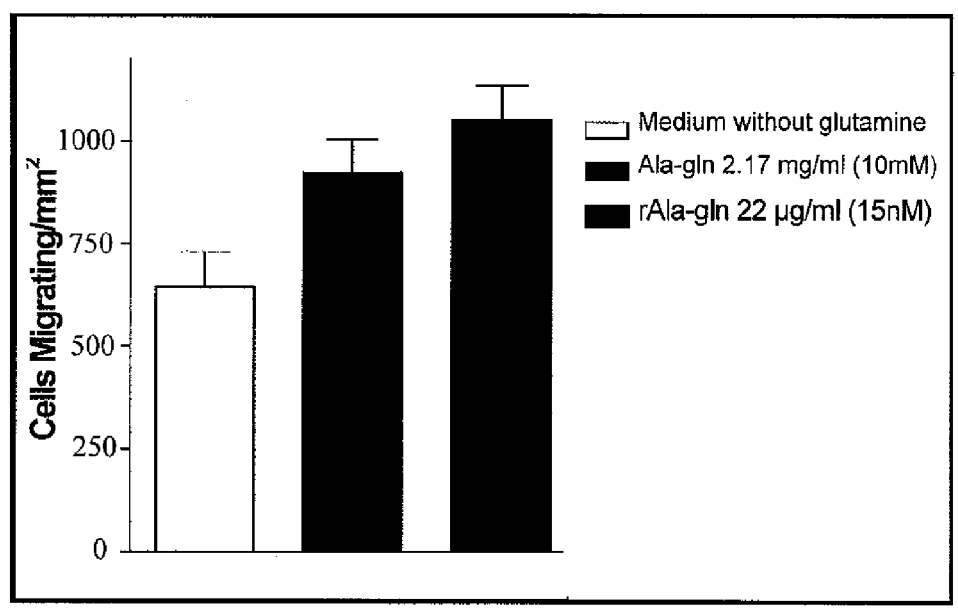

FIG. 5 demonstrates the enhancement of migration in IEC-6 cell monolayers by alanyl-glutamine chemically synthesized (Ala-gln) and biologically synthesized (rAla-gln) at 24 hours in vitro.

Figure 6:
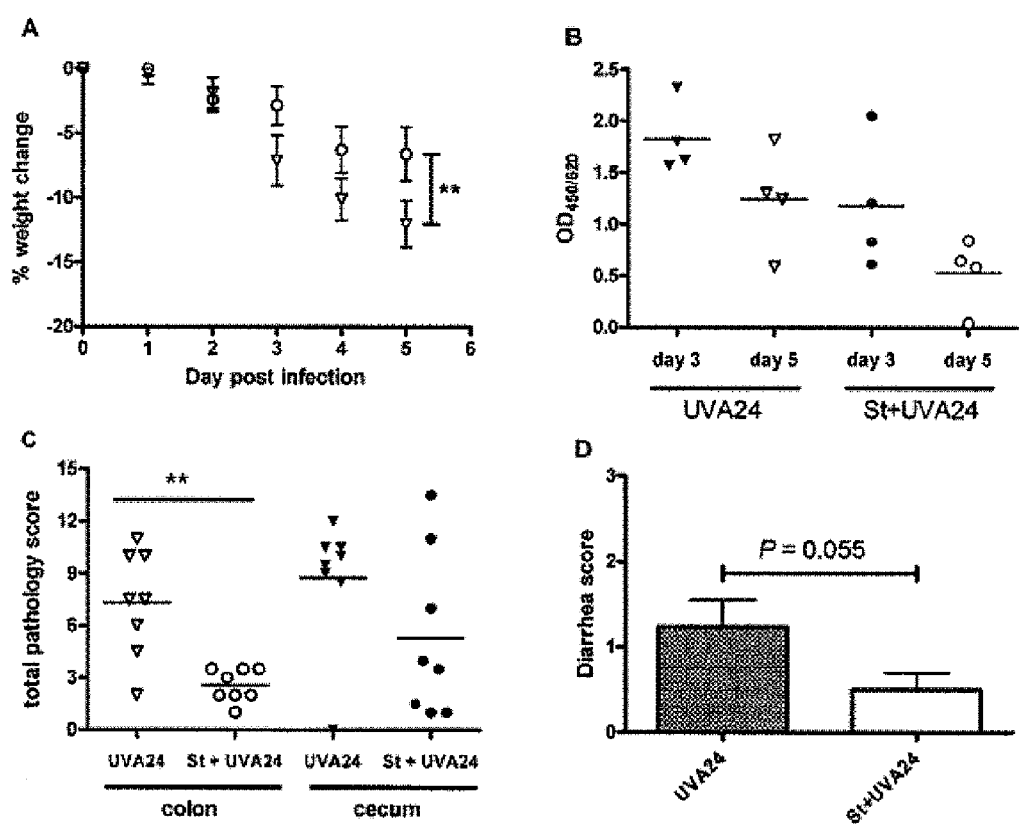

FIG. 6 illustrates that *Clostridium difficile* infection using UVA24 in mice is reduced by treatment with *Streptococcus thermophilus*. (A) Weight change was calculated relative to day 0 weight for each mouse (n≥17/group). *St. thermophilus* treated mice (circles) lost significantly less weight (P=0.004 using Wilks' Lambda multivariate test) than untreated control mice (triangles). Calculated data include final weights from mice that succumbed to infection or were euthanized for sample collection. (B) *St. thermophilus* treated mice (St+ UVA24) exhibited lower levels of TcdA/B in the cecal contents on days three and five compared to controls (UVA24) as detected using ELISA. (C) The colon of mice treated with *St. thermophilus* had significantly less pathology (P=0.006 using a Mann Whitney t-test) while cecal tissues from *St. thermophilus* treated mice showed less (P=0.279) compared to control three days post-infection. (D) The incidence of diarrhea on days three and four was scored as outlined in the methods and analyzed using an unpaired t-test.

Figure 7:
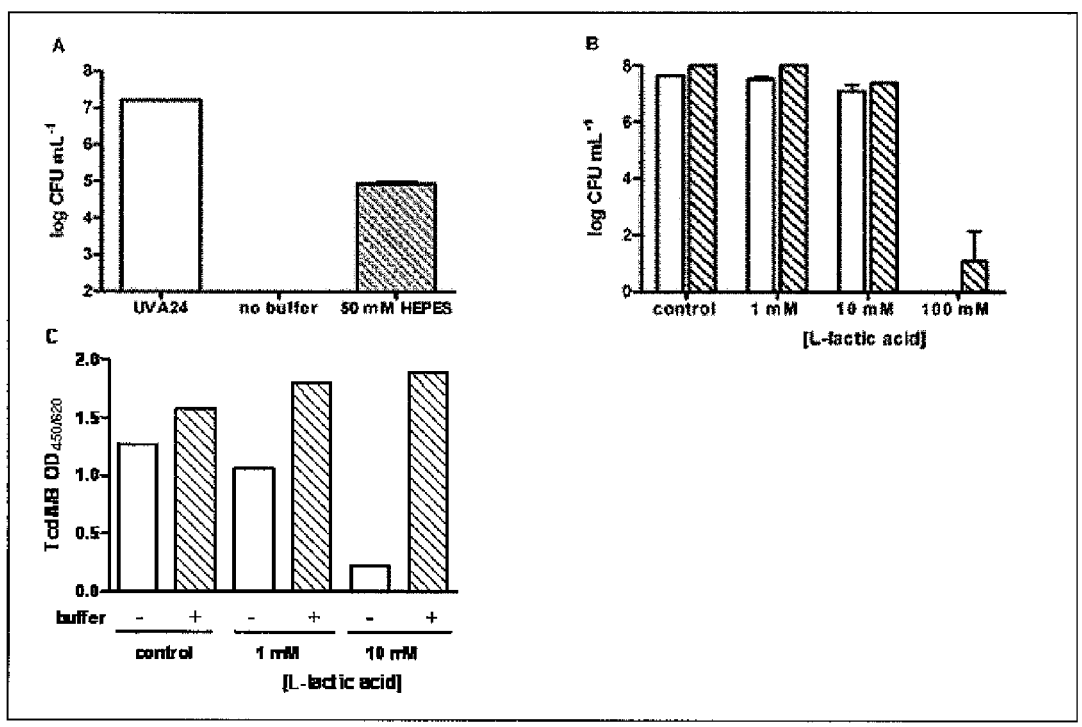

FIG. 7 demonstrates that *Clostridium difficile* growth is reduced by secreted components from *Streptococcus thermophilus*, namely lactic acid. (A) Filtered supernatants from *St. thermophilus* were added to BHI (50% v/v) in the absence or presence of HEPES buffer, inoculated (105 UVA24) incubated for 24 h and enumerated using plate counts. (B) Pure L-lactic acid was added to BHI at different concentrations, inoculated with *C. difficile*, grown for 24 h and bacteria enumerated. (C) Supernatants from 24 h growth of *C. difficile*±L-lactic acid±HEPES buffer (slashed bars) were tested for the presence of TcdA/B using ELISA.

Figure 8:
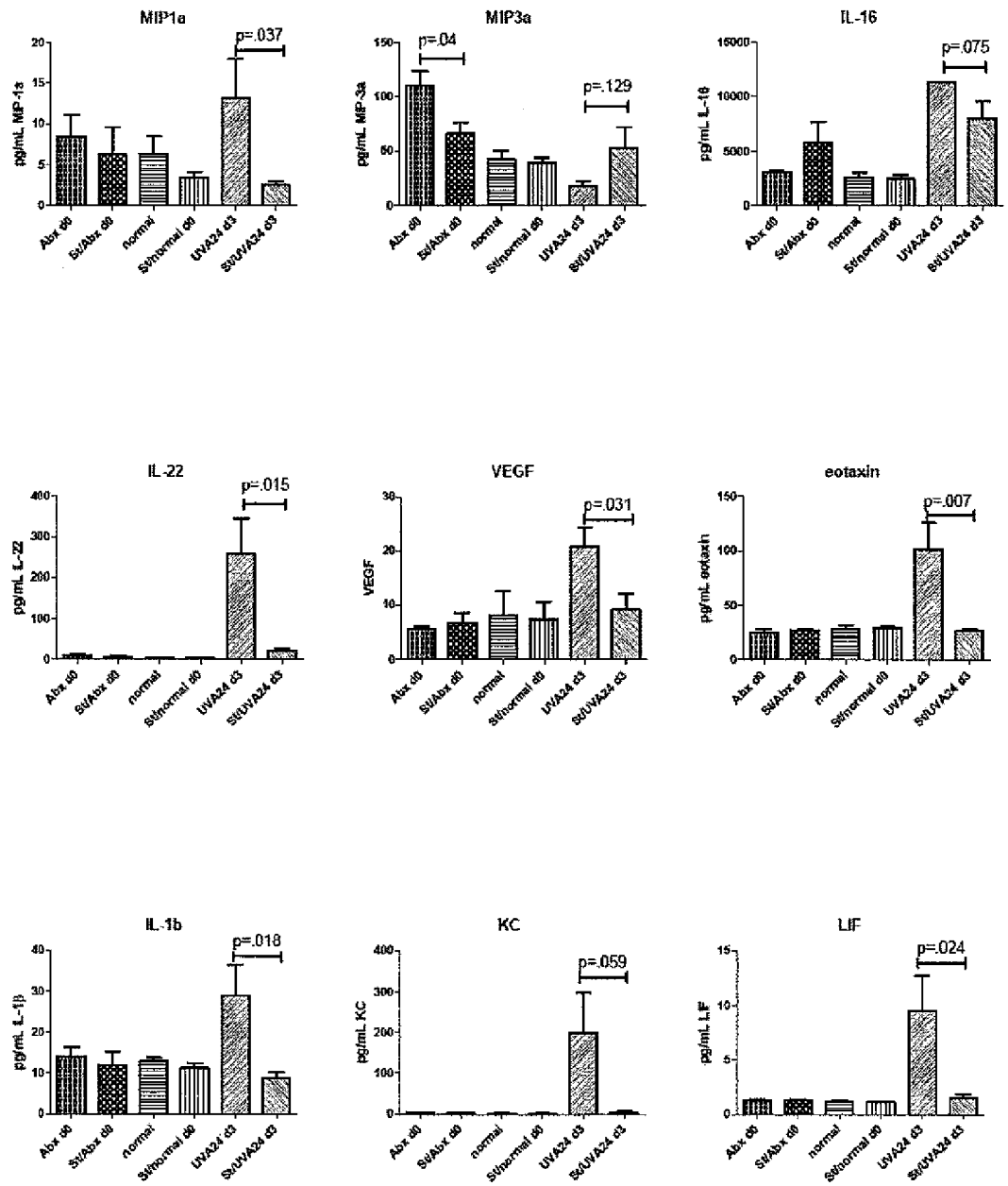

FIG. 8 reports cytokine response in the colon lysates of mice that were infected with *C. difficile* (UVA24)+/−*St. thermophilus* (St+UVA24) on day three post-infection, from colon lysates of mice that were exposed to antibiotics (Abx0)+/−*St. thermophilus* (St/Abx0), and from normal mice (normal)+/−*St. thermophilus* (St/normal 0) prior to infection.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Methods and compositions for targeted delivery of biotherapeutic agents are provided, including methods and compositions for delivery of AQ/AQR-rich peptides to the intestinal epithelium using bile-sensitive *St. thermophilus* bacteria. Such methods and compositions can be employed for the treatment or prevention of intestinal damage resulting from *C. difficile* infection. Bile-sensitive LAB can be provided prior to, during, and/or following antibiotic treatment to deliver therapeutic peptides to the intestinal tract while avoiding concerns of opportunistic infection. By surviving passage through the acidic environment of the stomach, bacteria disclosed herein can deliver therapeutic peptides directly to the small intestine. Accordingly, various bacteria, such as *St. thermophilus*, and methods of their use are provided which promote intestinal repair by delivering therapeutic agents or peptides to a subject in need thereof.

Bile-Sensitive Lactic Acid Bacteria

Methods and compositions are provided which result in targeted delivery of therapeutic agents to the gastrointestinal tract of a subject. As used herein, "released" refers to the discharge of components contained within the outer membrane of a cell into the environment. The term "released" is understood to encompass a discharge or partial discharge of naturally occurring or heterologous components (e.g. peptides) across the cellular membrane such that the released component no longer exists inside the cell. The term "released" is further understood to encompass a partial discharge of cellular components, for example, a release could result from permeabilization, or partial permeabilization, of the cellular membrane. For example, in specific embodiments, a microorganism of the invention is orally administered to a subject and survives passage through the stomach, wherein the microorganism is subsequently exposed to bile and releases intracellular material, including a biotherapeutic agent of interest. In some embodiments the release of biotherapeutic agent is sufficient to treat or prevent a gastrointestinal disorder.

As used herein, "bile sensitive" refers to the ability of a microorganism to become permeabilized and release some intracellular components following exposure to bile. The term "bile" refers to the dark green to yellowish brown fluid secreted by the liver of most vertabrates. As used herein, "bile" is mean to encompass bile salts and bile acids, including but not limited to cholic acid, dehydrocholic acid, chenodeoxycholic acid, deoxycholic acid, glycocholic acid, glycholic acid, glycodeoxycholic acid, taurocholic acid, lithocholic acid, taurodeoxycholic acid, chenodeoxycholic acid, ursodeoxycholic acid, sodium tauro-24,25-dihydrofusidate, sodium glycodihydrofusidate, polyoxyethylene-9-lauryl ether, or any combination thereof. As used herein, "exposure to bile" refers to a condition wherein the bacteria described herein are in contact with bile, or are present in the environment where bile exists. Exposure to bile can be for at least about 1 sec, about 5 sec, about 15 sec, about 30 sec, about 1 min, about 3 min, about 5 min, about 15 min, about 30 min, about 45 min, about 1 hour, about 2 hours, about 3 hours, about 4 hours, about 5 hours, or any time sufficient to permeabilize the membrane of bile-sensitive bacteria.

In some embodiments, a bile-sensitive microorganism does not survive exposure to bile. As used herein, "does not survive" refers to the condition of a microorganism, or part thereof, that is no longer able to reproduce or carry out metabolic functions. In certain embodiments, the environment of the gastrointestinal location desired for delivery of a biotherapeutic agent causes membrane permeabilization of the microorganism after which the organism does not survive.

Any microorganism of interest can be used in the methods and compositions described herein. In some embodiments, the microorganism comprises a bacterium. In specific embodiments, the microorganism comprises a probiotic bacterium. The term "probiotic" as used herein refers to "live microorganisms, which when administered in adequate amounts confer a health benefit on a host (FAO 2001: see the website at isapp.net/docs/ProbioticDefinition.pdf) at least one organism that contributes to the health and balance of the intestinal tract of a subject. In specific embodiments, it is also referred to as "friendly", "beneficial", or "good" bacteria, which when ingested by a subject assists in the maintenance of a healthy intestinal tract and assists in partially or completely alleviating one or more symptoms of an illness and/or disease.

In some embodiments, microorganisms described herein are lactic acid bacteria. As used herein, "lactic acid bacteria" is intended bacteria from a genus selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus*, and *Weissella* (Holzapfel et al. (2001) *Am. J. Clin. Nutr.* 73:365S-373S; Sneath, ed. (1986) *Bergey's Manual of Systematic Bacteriology* Vol 2, Lippincott, Williams and Wilkins, Hagerstown, Md.). In certain embodiments, the microorganisms to be used are Streptococci. In specific embodiments, the microorganisms to be used are *Streptococcus thermophilus*, for example, *St. thermophilus* LMD-9.

Bacteria disclosed herein can be designated Generally Recognized as Safe (GRAS) by the Food and Drug Administration. Those organisms designated as GRAS is considered safe by the FDA and are so exempted from the food additive tolerance requirements of the Federal Food, Drug, and Cosmetic Act. GRAS bacteria can be bile-sensitive and can be used for the targeted delivery of biotherapeutic agents.

The bacteria of the invention have been modified, for example genetically modified, to express a peptide of interest. As used herein, the terms "recombinant bacterium" or "recombinant bacterial cells" refer to a bacterium or plurality or bacterial cells that contain at least one genetic alteration, has been transformed with at least one gene of interest, and a cell or cells that are descended from a cell so altered and which comprises the genetic alteration or gene of interest. Accordingly, as used herein, the term "modified", or "genetically modified", or "genetic modification" refers to a genetic alteration, such as a deletion, addition, or substitution, of a nucleic acid. In certain embodiments, a modification produces a bacterium that is genetically different from the wild-type, or naturally occurring, bacterium. In some embodiments, the genetic alteration is an insertion of a coding sequence of interest into the bacterium.

The coding sequence may be homologous or heterologous to the bacteria. By "heterologous" is intended a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form, or the promoter is not the native promoter for the operably linked polynucleotide. In some embodiments, the heterologous polynucleotide sequence encodes an alanyl-glutamine (AQ) or alanyl-glutamine/arginine (AQR) rich peptide.

Therapeutic Agents

By "therapeutic agent" or "biotherapeutic agent" is meant a substance which cures, alleviates, removes or lessens the symptoms of, or prevents or reduces the possibility of contracting any disorder or malfunction of the human or animal body.

Biotherapeutic agents can be any peptide, polypeptide, protein, vaccine, cytokine, bacteriocin, carbohydrate, lipid, or any other substance that acts as a therapeutic agent when provided to a subject. The bacteria disclosed herein have been modified to express a therapeutic peptide for delivery to a specific location within the gastrointestinal tract. By therapeutic peptide is meant any peptide, such as an AQ/AQR rich peptide, that acts as a therapeutic agent when provided to a subject.

i. Alanyl-Glutamine Rich Peptides

Compositions and methods are provided which employ the various alanyl-glutamine rich peptides disclosed herein. As used herein, "alanyl-glutamine rich peptides" or "AQ rich peptides" or "ALA-GLN rich peptides" encompasses bio-synthesized peptides, oligopeptides, and proteins that have been modified to enhance their alanyl-glutamine and glutamine content. As used herein "alanyl-glutamine/arginine rich peptides" or "AQR rich peptides" or "ALA-GLN-ARG rich peptides" encompasses bio-synthesized peptides, oligopeptides, and proteins that have been modified to enhance their alanyl-glutamine/arginine or glutamine/arginine content. In some embodiments, the AQ rich peptides comprise $(GLN)_n$, $ALA(GLN)_n$, or $(ALA\_GLN)_n$, and derivatives thereof. These peptides may be used as individual peptides, or linked, thereby forming an oligopeptide or protein with repeating units of the peptide. Alternatively, the peptides may be linked to unlike peptides to form alternate peptides, oligopeptides, or proteins. In some instances, the peptides may be or linked to oligopeptides or proteins containing both like and unlike peptides. The peptides, oligopeptides, proteins or repeating units may contain a protease cleavage site or a targeting signal. Protease cleavage sites may include, for example, those sites recognized by trypsin or chymotrypsin. As used herein "AQ/AQR rich-related sequences" or "AQ/AQR rich polynucleotide sequences" refers to polynucleotide sequences encoding AQ or AQR (AQ/AQR) rich polypeptides. AQ/AQR content can be measured, for example, by sequencing or mass spectrometry, commonly known in the art. Examples of AQ/AQR rich polynucleotide sequences include SEQ ID NO: 1, 3, 5, 7, 9, or 11.

The symbol ALA is used herein to represent an abbreviation for alanine, the symbol GLN is the abbreviation for glutamine, and the symbol ALA-GLN is the dipeptide alanyl-glutamine. Additionally, as used herein, $ALA(GLN)_n$ designates a peptide having alanine in the terminal position and a number (n) of glutamine units attached, while (ALA-GLN)$_n$ indicates a peptide composed of n alanyl-glutamine subunits and (GLN)$_n$ indicates a peptide composed of n glutamine subunits. Further, "n" notes the number of subunits units in the peptide. Typically, the peptides of the invention contain between about 1 and 20 subunits or units (e.g. n is about 1 to about 20). As disclosed herein, a peptide may be an independent species or a subunit of oligopeptide or protein. AQ/AQR rich peptides of the invention include the polypeptide sequences set froth in SEQ ID NOS: 2, 4, 6, 8, 10, or 12, the nucleic acid sequences set forth in SEQ ID NOS1, 3, 5, 7, 9, or 11, and variants and fragments thereof. For purposes of the present invention, the terms "protein", "peptide units", and "polypeptide" are used interchangeably.

AQ rich activity or AQR rich activity, as used herein, refers to the ability of AQ/AQR rich peptides to inhibit cell apoptosis and reduce mucosal disruption. By "inhibit", "inhibiting", "reduce", or "reducing" cellular apoptosis or mucosal disruption is intended to mean, cellular or mucosal damage is statistically lower than the cellular or mucosal damage in an appropriate control. In particular embodiments, inhibiting cellular apoptosis or reducing mucosal damage according to the presently disclosed subject matter results in at least about a 95% decrease, at least about a 90% decrease, at least about a 80% decrease, at least about a 70% decrease, at least about a 60% decrease, at least about a 50% decrease, at least about a 40% decrease, at least about a 30% decrease, at least about a 20% decrease, at least about a 10% decrease, or at least about a 5% decrease of the cellular apoptosis or mucosal damage when compared to an appropriate control. In other embodiments, inhibiting cellular apoptosis or reducing mucosal damage results in a decrease of about 3% to about 15%, about 10% to about 25%, about 20% to about 35%, about 30% to about 45%, about 40% to about 55%, about 50% to about 65%, about 60% to about 75%, about 70% to about 90%, about 70% to about 80%, about 70% to about 85%, about 80% to about 95%, about 90% to about 100% when compared to an appropriate control. Methods to assay for the level of cellular apoptosis and mucosal damage are discussed elsewhere herein.

ii. Fragments and Variants

Depending on the context, "fragment" refers to a portion of the amino acid sequence of a polypeptide or protein, or polynucleotide encoding a portion of the amino acid sequence of a polypeptide or protein. Fragments may retain the activity of the original protein and hence, such "active" fragments include, for example, fragments of an AQ/AQR rich protein. A fragment of an AQ/AQR rich polynucleotide sequence, such as a fragment of SEQ ID NO: 1, 3, 5, 7, 9, or 11 that encodes an AQ/AQR rich peptide, may encode a protein fragment that is biologically active. Fragments of AQ/AQR rich proteins include fragments of SEQ ID NOS: 2, 4, 6, 8, 10 and 12. A biologically active nucleotide fragment can be prepared by isolating a portion of an AQ/AQR rich polynucleotide or polypeptide, expressing the encoded portion of the AQ/AQR rich peptide, and assessing the AQ/AQR level of the encoded portion of the AQ/AQR rich peptide. Fragments of AQ/AQR rich-related polynucleotides include fragments of SEQ ID NOS: 1, 3, 5, 7, 9, and 11. Fragments of AQ/AQR rich-related polynucleotides comprise at least about 15, about 20, about 50, about 75, about 100, about 200, about 250, about 300, about 350, about 400, about 450, about 500, about 550, about 600, about 650, about 700, about 750, about 800, about 850, about 900, about 950, about 1000 nucleotides or up to the total number of nucleotides present in a full-length AQ/AQR rich-related nucleotide sequence as disclosed herein.

Fragments of amino acid sequences include peptides comprising amino acid sequences sufficiently identical to or derived from the amino acid sequence of an AQ/AQR rich protein, or a partial-length protein and exhibiting at least one activity of an AQ/AQR rich protein (i.e. an activity associated with increased AQ/AQR content described elsewhere herein), but which include fewer amino acids than the full-length AQ/AQR rich proteins disclosed herein. A biologically active portion of a AQ/AQR rich protein can be a polypeptide that is, for example, about 10, about 25, about 50, about 100, about 150, about 200 contiguous amino acids in length, or up to the total number of amino acids present in a full-length AQ/AQR rich disclosed herein (i.e., of SEQ ID NO: 2, 4, 6, 8, 10, or 12). Such biologically active portions can be prepared by recombinant techniques and evaluated for one or more of the functional activities of a full length AQ/AQR rich protein, such as inhibiting cell apoptosis and reducing mucosal disruption. As used herein, a fragment comprises at least 5 contiguous amino acids of SEQ ID NOS: 2, 4, 6, 8, 10, or 12. The invention encompasses other fragments, however, such as any fragment of an AQ/AQR rich protein greater than about 6, about 7, about 8, about 9, about 10, about 20, about 50, about 100, about 200, about 300, about 400 or greater than about 500 amino acids.

In some embodiments bacteria are provided which have been modified to express variants of the AQ/AQR rich nucleotide and amino acid sequences provided elsewhere herein. By "variant" is intended a sufficiently identical sequence. Accordingly, the invention encompasses bacteria, modified to express AQ/AQR rich nucleic acid sequences that are sufficiently identical to the nucleotide sequences encoding AQ/AQR rich proteins in SEQ ID NOS: 2, 4, 6, 8, 10, or 12, or bacteria modified to express the nucleotide sequence of SEQ ID NOS: 1, 3, 5, 7, 9, or 11, or a complement thereof. Variants also include variant polypeptides encoded by the AQ/AQR rich polynucleotide sequences disclosed herein. In addition, polypeptides of the current invention have an amino acid sequence that is sufficiently identical to an amino acid sequence put forth in SEQ ID NOS: 2, 4, 6, 8, 10, or 12. By "sufficiently identical" is intended that one amino acid sequence or nucleotide sequence contains a sufficient or minimal number of equivalent or identical amino acid residues or nucleotides as compared to a second amino acid sequence or nucleotide sequence, thus providing a common structural domain and/or indicating a common functional activity, such as inhibiting cell apoptosis and reducing mucosal disruption. Conservative variants include those nucleotide sequences that differ due to the degeneracy of the genetic code.

In general, amino acid sequences or nucleotide sequences that have at least about 45%, 55%, or 65% identity, preferably at least about 70% or about 75% identity, more preferably at least about 80%, about 85% or about 90%, most preferably at least about 91%, about 92%, about 93%, about 94%, about 95%, about 95%, about 96%, about 97%, about 98%, about 99%, or about 99.5% sequence identity to any of the amino acid sequences of SEQ ID NOS: 2, 4, 6, 8, 10, or 12 or any of the nucleotide sequences of SEQ ID NOS: 1, 3, 5, 7, 9, or 11, respectively, are defined herein as sufficiently identical. Variant proteins encompassed by the present invention are biologically active, that is they retain the desired functional activity of the original AQ/AQR rich sequence, such as inhibiting cell apoptosis and reducing mucosal disruption. See, for example, Varcamonti et al. (2003) *Appl. Environ. Microbiol.* 69: 1287-1289. A biologically active variant of a protein may differ from that protein by as few as 1-15 amino acid residues, as few as 1-10, such as 6-10, as few as 5, as few as 4, 3, 2, or even 1 amino acid residue.

AQ/AQR rich polypeptides may be altered in various ways including amino acid substitutions, deletions, truncations, and insertions. Methods for mutagenesis and polynucleotide alterations are well known in the art. See, for example, Kunkel (1985) *Proc. Natl. Acad. Sci. USA* 82: 488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made. One skilled in the art will appreciate that the activity of an AQ/AQR rich polypeptide disclosed herein can be evaluated by routine screening assays, such as those described elsewhere herein.

For example, the AQ/AQR rich polypeptides disclosed herein may be altered to include a FLAG-tag epitope, such as DYKDDDDK (SEQ ID NO: 13) (Hopp, 1988, Bio/Technology, 6:1204-1210). Addition of the FLAG-tag epitope, can aid in detection and purification of the AQ/AQR rich peptides disclosed here. FLAG and 3×FLAG are useful in Western blotting, immunocytochemistry, immunoprecipitation, flow cytometry, protein purification, and in the study of protein-protein interactions, cell ultrastructure, and protein localization. These small hydrophilic tags can improve detection and purification of recombinant fusion proteins when used with specific and sensitive Anti-FLAG antibodies. The FLAG system can facilitate the study of low-abundance proteins and the optimization of difficult protein expression projects. The FLAG peptide includes a binding site for several specific monoclonal and polyclonal antibodies and conjugates, each with different recognition and binding characteristics. The FLAG peptide is likely to be accessible to antibodies and to cleavage by enterokinase (Ek). Given the small size of the FLAG-tag epitope, it is not expected that the addition of the epitope will affect activity, secretion, or transport of the peptides disclosed herein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

iii. Recombinant Expression Vectors

The nucleic acid molecules encoding the therapeutic agents of the present invention may be included in vectors, preferably expression vectors. "Vector" refers to a nucleic acid molecule capable of transporting another nucleic acid to which it has been linked. Expression vectors include one or more regulatory sequences and direct the expression of genes to which they are operably linked. By "operably linked" is intended that the nucleotide sequence of interest is linked to the regulatory sequence(s) such that expression of the nucleotide sequence is allowed (e.g., in an in vitro transcription/translation system or in a host cell when the vector is introduced into the host cell). The term "regulatory sequence" is intended to include controllable transcriptional promoters, operators, enhancers, transcriptional terminators, and other expression control elements such as translational control sequences (e.g., Shine-Dalgarno consensus sequence, initiation and termination codons). These regulatory sequences will differ, for example, depending on the host cell being used.

The vectors can be autonomously replicated in a host cell (episomal vectors), or may be integrated into the genome of a host cell, and replicated along with the host genome (non-episomal mammalian vectors). Integrating vectors typically contain at least one sequence homologous to the bacterial chromosome that allows for recombination to occur between homologous DNA in the vector and the bacterial chromosome. Integrating vectors may also comprise bacteriophage or transposon sequences. Episomal vectors, or plasmids are circular double-stranded DNA loops into which additional DNA segments can be ligated. Plasmids capable of stable maintenance in a host are generally the preferred form of expression vectors when using recombinant DNA techniques.

The expression constructs or vectors encompassed in the present invention comprise a nucleic acid construct of the invention in a form suitable for expression of the nucleic acid in a host cell. Expression in prokaryotic host cells is encompassed in the present invention. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., AQ/AQR rich peptides, mutant forms of AQ/AQR rich peptides, AQ/AQR rich fusion peptides, etc.).

Regulatory sequences include those that direct constitutive expression of a nucleotide sequence as well as those that direct inducible expression of the nucleotide sequence only under certain environmental conditions. A bacterial promoter is any DNA sequence capable of binding bacterial RNA polymerase and initiating the downstream (3') transcription of a coding sequence (e.g., structural gene) into mRNA. A promoter will have a transcription initiation region, which is usually placed proximal to the 5' end of the coding sequence. This transcription initiation region typically includes an RNA polymerase binding site and a transcription initiation site. A bacterial promoter may also have a second domain called an operator, which may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence.

An example of a gene activator protein is the catabolite activator protein (CAP), which helps initiate transcription of the lac operon in *Escherichia coli* (Raibaud et al. (1984) *Annu. Rev. Genet.* 18:173). Regulated expression may therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, p6 promoter, and a bacteriophage lambda promoter. Any suitable promoter can be used to carry out the present invention, including the native promoter or a heterologous promoter. Heterologous promoters may be constitutively active or inducible. A non-limiting example of a heterologous promoter is given in U.S. Pat. No. 6,242,194 to Kullen and Klaenhammer.

Sequences encoding metabolic pathway enzymes provide particularly useful promoter sequences. Examples include promoter sequences derived from sugar metabolizing enzymes, such as galactose, lactose (lac) (Chang et al. (1987) *Nature* 198:1056), and maltose. Additional examples include promoter sequences derived from biosynthetic enzymes such as tryptophan (trp) (Goeddel et al. (1980) *Nucleic Acids Res.* 8:4057; Yelverton et al. (1981) *Nucleic Acids Res.* 9:731; U.S. Pat. No. 4,738,921; EPO Publication Nos. 36,776 and 121, 775). The beta-lactamase (bla) promoter system (Weissmann, (1981) "The Cloning of Interferon and Other Mistakes," in Interferon 3 (ed. I. Gresser); bacteriophage lambda PL (Shimatake et al. (1981) *Nature* 292:128); the arabinose-inducible araB promoter (U.S. Pat. No. 5,028,530); and T5 (U.S. Pat. No. 4,689,406) promoter systems also provide useful promoter sequences. See also Balbas (2001) *Mol. Biotech.* 19:251-267, where *E. coli* expression systems are discussed.

In addition, synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac (Amann et al. (1983) *Gene* 25:167; de Boer et al. (1983) *Proc. Natl. Acad. Sci.* 80:21) and trc (Brosius et al. (1985) *J. Biol. Chem.* 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter can also be comprised of a bacteriophage promoter and an *E. coli* operator region (EPO Publication No. 267, 851).

The vector may additionally contain a gene encoding the repressor (or inducer) for that promoter. For example, an inducible vector of the present invention may regulate transcription from the Lac operator (LacO) by expressing the gene encoding the Lad repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., lambda CI857, rendering lambda pL thermo-inducible, or lambda CI+, rendering lambda pL chemo-inducible) may be employed.

In addition to a functioning promoter sequence, an efficient ribosome-binding site is also useful for the expression of the fusion construct. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) *Nature* 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in *Biological Regulation and Development: Gene Expression* (ed. R. F. Goldberger, Plenum Press, NY).

The therapeutic agents can also be secreted from the cell by creating chimeric DNA molecules that encode a protein comprising a signal peptide sequence fragment that provides for secretion of the AQ/AQR rich peptides in bacteria (U.S. Pat. No. 4,336,336). The signal sequence fragment typically encodes a signal peptide comprised of hydrophobic amino acids that direct the secretion of the protein from the cell. The protein is either secreted into the growth media (Gram-positive bacteria) or into the periplasmic space, located between the inner and outer membrane of the cell (Gram-negative bacteria). Preferably there are processing sites, which can be cleaved either in vivo or in vitro, encoded between the signal peptide fragment and the AQ/AQR rich peptide.

DNA encoding suitable signal sequences can be derived from genes for secreted bacterial proteins, such as the *E. coli* outer membrane protein gene (ompA) (Masui et al. (1983) *FEBS Lett.* 151(1):159-164; Ghrayeb et al. (1984) *EMBO J.*

3:2437-2442) and the *E. coli* alkaline phosphatase signal sequence (phoA) (Oka et al. (1985) *Proc. Natl. Acad. Sci.* 82:7212). Other prokaryotic signals include, for example, the signal sequence from penicillinase, Ipp, or heat stable enterotoxin II leaders.

Bacteria such as *St. thermophilus* generally utilize the start codon ATG, which specifies the amino acid methionine (which is modified to N-formylmethionine in prokaryotic organisms). Bacteria also recognize alternative start codons, such as the codons GTG and TTG, which code for valine and leucine, respectively. When they are used as the initiation codon, however, these codons direct the incorporation of methionine rather than of the amino acid they normally encode. *St. thermophilus* recognizes these alternative start sites and incorporates methionine as the first amino acid.

Typically, transcription termination sequences recognized by bacteria are regulatory regions located 3' to the translation stop codon and thus, together with the promoter, flank the coding sequence. These sequences direct the transcription of an mRNA that can be translated into the polypeptide encoded by the DNA. Transcription termination sequences frequently include DNA sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

The expression vectors will have a plurality of restriction sites for insertion of the coding sequence for the therapeutic agent so that it is under transcriptional regulation of the regulatory regions. Selectable marker genes that ensure maintenance of the vector in the cell can also be included in the expression vector. Preferred selectable markers include those that confer resistance to drugs such as ampicillin, chloramphenicol, erythromycin, kanamycin (neomycin), and tetracycline (Davies et al. (1978) *Annu. Rev. Microbiol.* 32:469). Selectable markers may also allow a cell to grow on minimal medium, or in the presence of toxic metabolite and may include biosynthetic genes, such as those in the histidine, tryptophan, and leucine biosynthetic pathways.

The regulatory regions may be native (homologous), or may be foreign (heterologous) to the host cell and/or the nucleotide sequence of the invention. The regulatory regions may also be natural or synthetic. Where the regulatory region is "foreign" or "heterologous" to the host cell, it is intended that the regulatory region is not found in the native cell into which the regulatory region is introduced. Where the regulatory region is "foreign" or "heterologous" to the nucleotide sequence encoding the therapeutic agent of the invention, it is intended that the regulatory region is not the native or naturally occurring regulatory region for the operably linked nucleotide sequence encoding a therapeutic agent of the invention. For example, the regulatory region may be derived from phage. While it may be preferable to express the sequences using heterologous regulatory regions, native or homologous regions may be used. Such constructs would be expected in some cases to alter expression levels of the therapeutic agent in the host cell. Thus, the phenotype of the host cell would be altered, even if a native peptide is being expressed.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Alternatively, the above-described components can be put together in transformation vectors. Transformation vectors are typically comprised of a selectable marker that is either maintained in a replicon or developed into an integrating vector, as described above.

Expression vectors or amino acid sequences of the invention may be introduced into host cells by methods known in the art. By "introducing" is intended introduction into prokaryotic cells via conventional transformation or transfection techniques, or by phage-mediated infection. As used herein, the terms "transformation," "transduction," "conjugation," and "protoplast fusion" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Cold Spring Harbor, N.Y.) and other laboratory manuals.

Bacterial cells used to produce the therapeutic agents or polypeptides of this invention are cultured in suitable media, as described generally in Sambrook et al. (1989) *Molecular Cloning, A Laboratory Manual* (2d ed., Cold Spring Harbor Laboratory Press, Cold Spring Harbor, N.Y.).

Bacterial strains encompassed by the present invention include those that are biologically pure cultures of a bacterium comprising at least one nucleotide or amino acid sequence of the present invention. These strains may include but are not limited to: *Lactobacillus, Bifidobacterium, Streptococcus thermophilus.*

As noted above, in one embodiment the therapeutic agent is an AQ/AQR rich polypeptide. Such polypeptide can be place in a DNA construct using heterologous or homologous regulatory regions. In particular, the AQ/AQR rich polypeptide can be expressed using the P6 promoter. While it can be expressed in any bile-sensitive microorganism, in one embodiment a genetically modified *St. thermophilus* bacterium is used to express the AQ/AQR rich polypeptide disclosed elsewhere herein.

Methods of Treatment and Prevention.

Methods are provided for treating and preventing gastrointestinal disorders in a subject comprising administration of a bacterium described elsewhere herein. In some embodiments, administration of a bacterium, for example, a *St. thermophilus* bacterium, can inhibit cell apoptosis and reduce mucosal disruption associated with toxin A released by *C. difficile* in a subject. In other embodiments, administration of a bile-sensitive bacterium expressing at least one therapeutic agent can inhibit cell apoptosis and reduce mucosal disruption associated with toxin A released by *C. difficile* in a subject. In some embodiments, methods for treating and/or preventing gastrointestinal disorders, treating and/or preventing symptoms associated with *C. difficile* infection, as well as treating pain locally in the intestines, in a subject are provided.

"Treatment" is herein defined as curing, healing, alleviating, relieving, altering, remedying, ameliorating, improving, or affecting the condition or the symptoms of a subject with a gastrointestinal disorder. The subject to be treated can be suffering from or at risk of developing a gastrointestinal disorder, including, for example, be suffering from a *C. difficile* infection or be at risk of developing a *C. difficile* infection. In one embodiment, the recombinant bile-sensitive bacterium can be administered prior to, concurrently with, or after the administration of an antibiotic to a patient.

Administration of the bacterium can be for either a prophylactic or therapeutic purpose. By "preventing" is intended that the bacterium is provided prophylactically, i.e., the bacterium is provided in advance of any symptom. The prophylactic administration of the recombinant bacterium serves to prevent or attenuate any subsequent symptom. When provided therapeutically, the bacterium is provided at or after the onset of a symptom. The therapeutic administration of the substance serves to attenuate any actual symptom.

By "subject" is intended animals. In specific embodiments, subjects are mammals, e.g., primates or humans. In other embodiments, subjects include domestic animals, such as a feline or canine, or agricultural animals, such as a ruminant, horse, swine, poultry, or sheep. In specific embodiments, the subject undergoing treatment with the pharmaceutical formulations of the invention is a human. In some embodiments, the human undergoing treatment can be a newborn, infant, toddler, preadolescent, adolescent or adult. The subjects of the invention may be suffering from the symptoms of a gastrointestinal disorder or may be at risk for a gastrointestinal disorder (e.g. a subject that has undergone antibiotic treatment).

Gastrointestinal Disorders

The methods of the invention relate to treatment and/or prevention of gastrointestinal disorders. As used herein, the term " gastrointestinal disorder" or "disorder of the gastrointestinal tract" refers to a disease of the gastrointestinal tract or bowel. Gastrointestinal disorders include, for example, bacterial infections caused by various microorganisms including viruses such as rotavirus, cytomegalovirus, enteric adenovirus, Norwalk virus, picornavirus, adenovirucoronavirus, Calicivirus (family Caliciviridae), and bovine viral diarrhea virus; bacteria, such asenterotoxigenic and invasive *Escherichia coli*, *Shigella*, *Salmonella*, *Vibrio bacteria* (e.g. *Vibrio cholerae*), *Clostridium difficile*, *Clostridium perfringens*, *Enterococcus faecium*, *Enterococcus faecalis*, *Staphylococcus aureus*, and *Campylobacter jejuni*; protozoa, such as *Microsporridia* spp., *Cryptospordia* spp. (e.g. *Cryptosporidium parvum*), *Isospora belli*, *Blastocystis hominis*, *Dientamoeba fragilis*, *Balantinium coli*, *Isopora belli*, *Cylclospora cayetanensis*, *Enterocytozoon bieneusi*, *Entamoeba histolytica*, *Giardia lamblia* (also called *Lamblia intestinalis*) and *Encephalitozoon intestitnalis*; and helminthes, such as *Strongyloides stercoralis*. Antibiotic-mediated disruption of the normal gastrointestinal flora can lead to gastrointestinal disorders including fungal infections, such as invasive candidiasis, or antibiotic-associated colitis caused by *C. difficile*.

The methods and compositions of the invention relate to treatment of inflammatory gastrointestinal disorders. As used herein, the term "inflammatory gastrointestinal disorder" or "inflammatory disorder of the gastrointestinal tract" refers to a disease of the gastrointestinal tract or bowel that is mediated by the immune system or cells of the immune system. Inflammatory gastrointestinal disorders include, for example, inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease, as well as diarrhea, bloating, flatulence, abdominal cramping, abdominal pain, or constipation. In certain embodiments, the methods of the invention relate to the treatment or prevention of obesity, or the symptoms of obesity including, IBD, diarrhea, bloating, flatulence, abdominal cramping, abdominal pain, or constipation. See, for example, Kadooka Y, et. al. (2010) *Eur J Clin Nutr.* 64(6):636-43, herein incorporated by reference.

In some embodiments, the decrease in inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T and B cell immunity; stimulation of a helper T cell 1 (Th1) cytokine pattern (increased IL-1, IL-2, IFN-gamma, IL-12, TNF-alpha; human leukocyte antigen-Dr (HLA-Dr) expression); suppression of inflammation or production of systemic and mucosal inflammatory mediators (including cytokines and/or chemokines); reduction of sensitization by reducing total and/or allergen-specific IgE; reduction of the production of allergic cytokines; reduction of a Th2 supporting immunoglobulin profile; and combinations thereof.

As used herein, the term "proinflammatory cytokine" refers to an immunoregulatory cytokine that favors inflammation. Proinflammatory cytokines of the invention include IL1-alpha, IL1-beta, TNF-alpha, IL-2, IL-3, IL-6, IL-7, IL-9, IL-12, IL-16, IL-17, IL-18, IL-22, VEGF, eotaxin, KC, TNF-alpha, MIP1a, MIP3a, LT, LIF, Oncostatin, or IFN-alpha, IFN-beta, IFN-gamma.

Methods and compositions of the invention include those which decrease proinflammatory cytokine production, which may decrease or prevent an inflammatory response or prevent or treat an inflammatory disorder of the gastrointestinal tract. As used herein, a decrease in the level of pro-inflammatory cytokine production comprises any statistically significant decrease in the level of pro-inflammatory cytokine production in a subject when compared to an appropriate control. Such decreases can include, for example, at least a 5%, 10%, 20%, 30%, 40%, 50%, 60%, 70%, 80%, 90%, or 100% decrease in the level of proinflammatory cytokines Methods to assay for cytokine levels are known and include, for example Leng, 2008, *J Gerontol A Biol Sci Med Sci* 63(8): 879-884. Methods to assay for the production of pro-inflammatory cytokines include multiplex bead assay, ELISPOT and flow cytometry. See, for example, Maecker, 2005, *BMC Immunology* 6:13.

As used herein "cellular apoptosis" or "apoptosis" refers to programmed cell death essential to maintain the balance between cell proliferation and cell elimination. Toxic agents such as chemotherapeutic drugs, ionizing radiation, microorganisms, and immune-mediated reactions are known to increase the rate of apoptosis in intestinal epithelial cells, resulting in epithelial damage. Apoptosis is implemented by a family of intracellular cysteine proteases, called capsases. In *C. difficile*-associated diarrhea, toxin A released by *C. difficile* can act to induce apoptosis in intestinal epithelial cells, mast cells, and endothelial cells, which can contribute to intestinal mucosal disruption. As used herein, "mucosal disruption" refers to irritation, inflammation, erosion, ulceration, epithelial damage, edema, or neutrophil infiltration of mucosal cells. Methods to assay for cellular apoptosis and mucosal disruption are described elsewhere herein. It is understood that administration of the bacterium can promote intestinal wound healing. Wound healing can be determined by measuring cellular apoptosis and mucosal disruption as disclosed elsewhere herein, for example by measuring cell migration.

In some embodiments, administration of the bacterium of the invention results in inhibition of caspase 8 activation induced by TxA, without interfering with caspase 6 or 9 activation. In other embodiments, administration of the bacterium of the invention results in induction of Heat Shock Proteins (HSPs), such as HSP 72.

Pharmaceutical Composition

In some embodiments, bile-sensitive bacterial strains expressing a therapeutic agent of the invention are administered to a subject in the form of a nutraceutical composition such as a nutritional supplement and/or food additive. In specific embodiments, the pharmaceutical composition comprises a bacterium that has been modified to express an AQ/AQR rich peptide (such as the polynucleotide and polypeptide set forth in SEQ ID NO: 1 and 2). In other embodiments, the extracts are administered to a subject in the form of a pharmaceutical composition. The administration may comprise a single dose or multiple dose administration, as described elsewhere herein.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins. The pharmaceutical composition may be delivered as a food product for human consumption or a feed product for consumption by agricultural or domestic animals.

As used herein, the term "pharmaceutical composition" could be formulated as a food composition, a dietary supplement, a functional food, a medical food or a nutritional product as long as the required effect is achieved, i.e. treatment or prevention of a gastrointestinal disorder. Said food composition may be chosen from the group consisting of beverages, yogurts, juices, ice creams, breads, biscuits, crackers, cereals, health bars, spreads and nutritional products. The food composition may further comprise a carrier material, wherein said carrier material is chosen from the group consisting of lactic acid fermented foods, fermented dairy products, resistant starch, dietary fibers, carbohydrates, proteins, and glycosylated proteins.

The pharmaceutical composition according to the invention, used according to the invention or produced according to the invention may also comprise other substances, such as an inert vehicle, or pharmaceutical acceptable adjuvants, carriers, preservatives etc., which are well known.

The present disclosure also includes combinations of the bacteria disclosed herein with one another, and/or with one or more other agents useful in the treatment of a disorder of the gastrointestinal tract. For example, bacteria of the invention may be administered in combination with effective doses of conventional antibiotics, including metronidazole, cephalexin, ciprofloxacin, levofloxacin, moxifloxacin, gemifloxacin, balofloxacin, gatifloxacin, grepafloxacin, pazufloxacin, sparfloxacin, temafloxacin, enoxacin, fleroxacin, lomefloxacin, nadifloxacin, norfloxacin, ofloxacin, pefloxacin, rufloxacin, trovofloxacin, tosufloxacin, clindamycin, tetracycline, chloramphenicol, cefoxitin, cefmetazole, cefotetan, doxycycline, erythromycin, imipenem, meropenem, ticarcillin, pipercillin, mezocillin, tazobactam, ampicillin, and combinations thereof The term "administration in combination" refers to both concurrent and sequential administration of the active agents. The combination therapies are not limited to the agents provided herein, but include any composition for the treatment of disorders.

Therapeutically effective amount By "therapeutically effective dose," "therapeutically effective amount," or "effective amount" is intended an amount of the bacterium of the invention that, when administered to a subject, treats or prevents a gastrointestinal disorder. For example, administration of a therapeutically effective amount of a bacterium of the invention can inhibit cell apoptosis and reduce mucosal disruption in a subject having a C. difficile infection. "Positive therapeutic response" refers to, for example, improving the condition of at least one of the symptoms of a gastrointestinal disorder.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of recombinant bacteria will vary depending upon such factors as the patient's age, weight, height, sex, general medical condition and previous medical history. In specific embodiments, it may be desirable to administer the bacterium in the range of about $10^4$ to about $10^{12}$ CFU, about $10^5$ to about $10^{11}$ CFU, about $10^6$ to about $10^{10}$ CFU, about $10^8$ to about $10^{10}$ CFU or about $10^8$ to about $10^{12}$ CFU.

In some embodiments of the invention, the method comprises administration of multiple doses of the bacterium. The method may comprise administration of about 1, about 2, about 3, about 4, about 5, about 6, about 7, about 8, about 9, about 10, about 15, about 20, about 25, about 30, about 35, about 40, or more therapeutically effective doses of a composition comprising the bacterium as described herein. In some embodiments, doses are administered over the course of about 1 day, about 2 days, about 3 days, about 4 days, about 5 days, about 6 days, about 7 days, about 10 days, about 14 days, about 21 days, about 30 days, or more than about 30 days. The frequency and duration of administration of multiple doses of the compositions is such as to reduce or prevent an inflammatory response and thereby treat or prevent a gastrointestinal disorder. Moreover, treatment of a subject with a therapeutically effective amount of the recombinant bacterium of the invention can include a single treatment or can include a series of treatments. It will also be appreciated that the effective dosage of a bacterium used for treatment may increase or decrease over the course of a particular treatment. Changes in dosage may result and become apparent from the results of diagnostic assays for detecting inflammation known in the art and described herein.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Deposits

Applicant made a deposit of *Streptococcus thermophilus* LMD-9 with the American Type Culture Collection (ATCC), Manassas, Va. 20110 USA, ATCC Accession Number PTA-11888. Applicants further made a deposit of *Streptococcus thermophilus* NCK2071 under ATCC Accession Number PTA-11889, *Streptococcus thermophilus* NCK2072 under ATCC Accession Number PTA-11890, and *Streptococcus thermophilus* NCK2073 under ATCC Deposit No. ATCC Accession Number PTA-11891.

The bacterial cultures deposited with the ATCC were taken from the deposit maintained by North Carolina State University, 100 Schaub Hall, Campus Box 7624, Raleigh, N.C., 27695 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce.

In light of the description provided above, the following embodiments are provided:

According to a first aspect, there is provided a *Streptococcus thermophilus* bacterium that is modified to express a heterologous polypeptide, wherein said heterologous polypeptide is released from said bacterium following exposure to bile.

In one embodiment, the heterologous polypeptide is a therapeutic polypeptide. In a specific embodiment, the heterologous polypeptide is an Alanine-Glutamine rich peptide.

In a further embodiment, the Alanine-glutamine rich peptide is selected from the group consisting of:
a) a peptide comprising the amino acid sequence having at least about 70%, about 80%, about 90%, about 95%, about 97%, about 98%, or about 99% sequence identity to the amino acid sequence as set forth in SEQ ID NO:2 or 8;
b) a peptide comprising the amino acid sequence having at least about 70%, about 80%, about 90%, about 95%, about 97%, about 98%, or about 99% sequence identity to the amino acid sequence as set forth in SEQ ID NO:4 or 10;
c) a peptide comprising the amino acid sequence having at least about 70%, about 80%, about 90%, about 95%, about 97%, about 98%, or about 99% sequence identity to the amino acid sequence as set forth in SEQ ID NO:6 or 12;
d) a peptide encoded by a nucleic acid comprising the sequence of at least one of SEQ ID NOs: 1, 3, 5, 7, 9, or 11 or a nucleotide having at least about 70%, about 80%, about 90%, about 95%, about 96%, about 97%, about 98%, or about 99% sequence identity to at least one of SEQ ID NOs: 1, 3, 5, 7, 9, or 11; and
e) a peptide which differs from any one of SEQ ID NOs: 2, 4, 6, 8, 10, or 12 by one or several amino acids.

In a further embodiment, Alanine-Glutamine rich peptide is selected from the group consisting of SEQ ID NO: 2, 4, 6, 8, 10, or 12.

In a further embodiment, the bacterium of any one of the previous embodiments does not survive said bile exposure.

In a further embodiment, the bacterium of any one of the previous embodiments is *Streptococcus thermophilus* LMD-9, *Streptococcus thermophilus* NCK2071, *Streptococcus thermophilus* NCK2072, or *Streptococcus thermophilus* NCK2073.

In a second aspect, a method of making a *Streptococcus thermophilus* bacterium is provided, said method comprising genetically modifying said bacterium to express a heterologous polypeptide, wherein said polypeptide is released from said bacterium following exposure to bile.

In a further embodiment, said heterologous polypeptide is an Alanine-Glutamine rich peptide.

In a further embodiment, the Alanine-glutamine rich peptide is selected from the group consisting of:
a) a peptide comprising the amino acid sequence having at least about 70%, about 80%, about 90%, about 95%, about 97%, about 98%, or about 99% sequence identity to the amino acid sequence as set forth in SEQ ID NO:2 or 8;
b) a peptide comprising the amino acid sequence having at least about 70%, about 80%, about 90%, about 95%, about 97%, about 98%, or about 99% sequence identity to the amino acid sequence as set forth in SEQ ID NO:4 or 10;
c) a peptide comprising the amino acid sequence having at least about 70%, about 80%, about 90%, about 95%, about 97%, about 98%, or about 99% sequence identity to the amino acid sequence as set forth in SEQ ID NO:6 or 12;
d) a peptide encoded by a nucleic acid comprising the sequence of at least one of SEQ ID NOs: 1, 3, 5, 7, 9, or 11, or a nucleotide having at least about 70%, about 80%, about 90%, about 95%, about 96%, about 97%, about 98%, or about 99% sequence identity to at least one of SEQ ID NOs: 1, 3, 5, 7, 9, or 11; and
e) a peptide which differs from any one of SEQ ID NOs: 2, 4, 6, 8, 10, or 12 by one or several amino acids.

In a further embodiment, said Alanine-Glutamine rich peptide is selected from the group consisting of SEQ ID NO: 2, 4, 6, 8, 10, or 12.

In a further embodiment, said bacterium does not survive said bile exposure.

In a further embodiment, the bacterium of any one of the previous embodiments is *Streptococcus thermophilus* LMD-9, *Streptococcus thermophilus* NCK2071, *Streptococcus thermophilus* NCK2072, or *Streptococcus thermophilus* NCK2073.

According to a third aspect, there is provided a method of delivering a heterologous polypeptide to a subject, said method comprising orally administering to a subject the bacterium according to any one of the previous embodiments.

According to a fourth aspect, there is provided a method of treating or preventing a disorder in a subject, said method comprising orally administering to a subject a therapeutically effective amount of the bacterium according to any one of the previous embodiments.

In a further embodiment, the subject is an animal, more specifically a mammal.

In another embodiment the subject is a human.

In a further embodiment the subject is a domestic animal.

In a still further embodiment, the subject is an agricultural animal.

In a further embodiment the subject has a gastrointestinal disorder.

In a further embodiment, the disorder is a bacterial infection, more specifically a *Clostridium difficile* infection.

In a further embodiment, the bacterium is administered in a therapeutically effective amount, wherein the therapeutically effective amount of the bacterium is about $10^8$ to $10^{12}$ CFU/day.

According to a fifth aspect, there is provided a pharmaceutical composition comprising the bacterium described herein.

According to a sixth aspect, there is provided a food or feed product comprising the recombinant bacterium described herein.

In a further embodiment, the food product is a dairy food product.

According to a seventh aspect, there is provided the bacterium described herein for use as a medicament.

According to an eighth aspect, there is provided the bacterium described herein for use in treating or preventing a disorder in a subject.

In a further embodiment, the disorder is a gastrointestinal disorder.

In a further embodiment, the bacterium is for use in treating a bacterial infection, more specifically a *Clostridium difficile* infection.

In an alternative embodiment, the disorder is an inflammatory disorder.

The bacterium is for use in decreasing inflammation. In one embodiment, the bacterium decreases the production of one or more pro-inflammatory cytokines in said subject, more specifically, the bile-sensitive *St. thermophilus* bacterium decreases the production of MIP1a, MIP3a, IL-16, IL-22, VEGF, eotaxin, IL-1b, KC, or LIF.

It will be understood that the bacterium is provided in a therapeutically effective amount, wherein the therapeutically effective amount of the bacterium is about $10^8$ to $10^{12}$ CFU/day.

According to a ninth aspect, there is provided the use of a bacterium described herein as a medicament.

In one embodiment, the medicament is for treating or preventing a disorder in a subject.

In one embodiment the medicament is for the treatment of a gastrointestinal disorder.

In a further embodiment, the disorder is a bacterial infection, more specifically a *Clostridium difficile* infection.

In an alternative preferred embodiment, the disorder is an inflammatory disorder.

The medicament is for decreasing inflammation. In one embodiment, the medicament decreases the production of one or more pro-inflammatory cytokines in said subject, more specifically, the bile-sensitive *St. thermophilus* bacterium decreases the production of MIP1a, MIP3a, IL-16, IL-22, VEGF, eotaxin, IL-1b, KC, or LIF.

According a tenth aspect a method of treating an inflammatory disorder of the gastrointestinal tract of a subject is provided comprising, administering to a subject a therapeutically effective amount of an isolated bile-sensitive *Streptococcus thermophilus* bacterium.

According to an eleventh aspect a method of decreasing inflammation in a subject is provided comprising administering to a subject a therapeutically effective amount of an isolated bile-sensitive *Streptococcus thermophilus* bacterium.

In a further embodiment, the subject has an inflammatory gastrointestinal disorder, more specifically a *Clostridium difficile* infection.

In another embodiment, the bile-sensitive *St. thermophilus* bacterium decreases the production of one or more pro-inflammatory cytokines in said subject, more specifically, the bile-sensitive *St. thermophilus* bacterium decreases the production of MIP1a, MIP3a, IL-16, IL-22, VEGF, eotaxin, IL-1b, KC, or LIF.

It will be understood that the bacterium is provided in a therapeutically effective amount, wherein the therapeutically effective amount of the bacterium is about $10^8$ to $10^{12}$ CFU/day.

In light of the description provided above, the following embodiments are further provided:

1. A *Streptococcus thermophilus* bacterium that is modified to express a heterologous polypeptide, wherein said heterologous polypeptide is released from said bacterium following exposure to bile.

2. The bacterium of embodiment 1, wherein said heterologous polypeptide is a therapeutic polypeptide.

3. The bacterium of embodiment 1 or 2, wherein said heterologous polypeptide is an Alanine-Glutamine rich peptide.

4. The bacterium of embodiment 3, wherein said Alanine-glutamine rich peptide is selected from the group consisting of:
  a) a peptide comprising the amino acid sequence having at least 70%, 80%, 90%, 95%, 97%, 98%, or 99% sequence identity to the amino acid sequence as set forth in SEQ ID NO:2 or 8;
  b) a peptide comprising the amino acid sequence having at least 70%, 80%, 90%, 95%, 97%, 98%, or 99% sequence identity to the amino acid sequence as set forth in SEQ ID NO:4 or 10;
  c) a peptide comprising the amino acid sequence having at least 70%, 80%, 90%, 95%, 97%, 98%, or 99% sequence identity to the amino acid sequence as set forth in SEQ ID NO:6 or 12;
  d) a peptide encoded by a polynucleotide comprising a nucleotide sequence as set forth in any SEQ ID NOs: 1, 3, 5, 7, 9, or 11; and
  e) a peptide encoded by a polynucleotide comprising a nucleotide sequence having at least about 70%, about 80%, about 90%, about 95%, about 96%, about 97%, about 98%, or about 99% sequence identity to at least one of SEQ ID NOs: 1, 3, 5, 7, 9, or 11.

5. The bacterium of embodiment 3, wherein said Alanine-Glutamine rich peptide is selected from the group consisting of SEQ ID NO: 2, 4, 6, 8, 10, or 12.

6. The bacterium of any one of embodiment 1-5, wherein said bacterium does not survive said bile exposure.

7. The bacterium of any one of embodiment 1-6, wherein said *Streptococcus thermophilus* is selected from the group consisting of:
  a) *Streptococcus thermophilus* LMD-9, having been deposited under ATCC Accession Number ATCC-XXXX;
  b) *Streptococcus thermophilus* NCK2071, having been deposited under ATCC Accession Number ATCC-XXXX;

c) *Streptococcus thermophilus* NCK2072, having been deposited under ATCC Accession Number ATCC-XXXX;
d) *Streptococcus thermophilus* NCK2073, having been deposited under ATCC Accession Number ATCC-XXXX; and
e) a probiotic *Streptococcus thermophilus* bacterium.

8. A method of making a *Streptococcus thermophilus* bacterium, said method comprising genetically modifying said bacterium to express a heterologous polypeptide, wherein said polypeptide is released from said bacterium following exposure to bile.

9. The method of embodiment 8, wherein said heterologous polypeptide is an Alanine-Glutamine rich peptide.

10. The method of embodiment 8 or 9, wherein said Alanine-Glutamine rich peptide is selected from the group consisting of:
a) a peptide comprising the amino acid sequence having at least 70%, 80%, 90%, 95%, 97%, 98%, or 99% sequence identity to the amino acid sequence as set forth in SEQ ID NO:2 or 8;
b) a peptide comprising the amino acid sequence having at least 70%, 80%, 90%, 95%, 97%, 98%, or 99% sequence identity to the amino acid sequence as set forth in SEQ ID NO:4 or 10;
c) a peptide comprising the amino acid sequence having at least 70%, 80%, 90%, 95%, 97%, 98%, or 99% sequence identity to the amino acid sequence as set forth in SEQ ID NO:6 or 12;
d) a peptide encoded by a polynucleotide comprising a nucleotide sequence as set forth in any SEQ ID NOs: 1, 3, 5, 7, 9, or 11; and
e) a peptide encoded by a polynucleotide comprising a nucleotide sequence having at least about 70%, about 80%, about 90%, about 95%, about 96%, about 97%, about 98%, or about 99% sequence identity to at least one of SEQ ID NOs: 1, 3, 5, 7, 9, or 11.

11. The method of embodiments 8 or 9, wherein said Alanine-Glutamine rich peptide is selected from the group consisting of SEQ ID NO: 2, 4, 6, 8, 10, or 12.

12. The method of any one of embodiments 8-11, wherein said bacterium does not survive said bile exposure.

13. The method of any one of embodiments 8-12, wherein said *Streptococcus thermophilus* is selected from the group consisting of:
a) *Streptococcus thermophilus* LMD-9, having been deposited under ATCC Accession Number PTA-11888;
b) *Streptococcus thermophilus* NCK2071, having been deposited under ATCC Accession Number PTA-11889;
c) *Streptococcus thermophilus* NCK2072, having been deposited under ATCC Accession Number PTA-11890;
d) *Streptococcus thermophilus* NCK2073, having been deposited under ATCC Accession Number PTA-11891; and
e) a probiotic *Streptococcus thermophilus* bacterium.

14. A method of delivering a heterologous polypeptide to a subject, said method comprising orally administering to a subject the bacterium according to any one of embodiments 1-7.

15. A method of treating or preventing a disorder in a subject, said method comprising orally administering to a subject a therapeutically effective amount of the bacterium according to any one of embodiments 1-7.

16. The method of embodiment 14 or 15, wherein said subject is an animal.

17. The method of embodiment 16, wherein said subject is a mammal.

18. The method of embodiment 17, wherein said subject is a human.

19. The method of embodiment 16, wherein said subject is a domestic animal.

20. The method of embodiment 16, wherein said subject is an agricultural animal.

21. The method of any one of embodiments 15-20, wherein said disorder is a gastrointestinal disorder.

22. The method of any one of embodiments 15-20, wherein said disorder is a bacterial infection.

23. The method of embodiment 22, wherein said bacterial infection is a *Clostridium difficile* infection.

24. The method of any one of embodiments 14-23, wherein said therapeutically effective amount of the bacterium is about $10^8$ to $10^{12}$ CFU/day.

25. A pharmaceutical composition comprising the bacterium according to any one of embodiments 1-7.

26. A food or feed product comprising the bacterium according to any one of embodiments 1-7.

27. The food product of embodiment 24, wherein said food product is a dairy food product.

28. The bacterium according to any one of embodiments 1-7 for use as a medicament.

29. The bacterium according to any one of embodiments 1-7 for use in treating or preventing a disorder in a subject.

30. The bacterium for use according to embodiment 28 or 29, wherein said disorder is a bacterial infection.

31. The bacterium for use according to embodiment 30, wherein said bacterial infection is a *Clostridium difficile* infection in a subject.

32. The bacterium for use according to any one of embodiments 28-31, wherein said bacterium is formulated to be administered to a subject in a therapeutically effective amount, wherein the therapeutically effective amount of the bacterium is about $10^8$ to $10^{12}$ CFU/day.

33. Use of a bacterium according to any one of embodiments 1-7 as a medicament.

34. The use of a bacterium according to embodiment 33, wherein the medicament is for treating or preventing a disorder in a subject.

35. The use of a bacterium according to embodiment 34, wherein said disorder is a bacterial infection.

36. The use of a bacterium according to embodiment 35, wherein said bacterial infection is a *Clostridium difficile* infection.

37. A method of treating an inflammatory disorder of the gastrointestinal tract of a subject comprising, administering to a subject a therapeutically effective amount of an isolated bile-sensitive *Streptococcus thermophilus* bacterium.

38. A method of decreasing inflammation in a subject comprising administering to a subject a therapeutically effective amount of an isolated bile-sensitive *Streptococcus thermophilus* bacterium.

39. The method of embodiments 37 or 38, wherein said subject has an inflammatory gastrointestinal disorder.

40. The method of embodiment 39, wherein said inflammatory gastrointestinal disorder is a *Clostridium difficile* infection.

41. The method of any one of embodiments 37-40, wherein said bile-sensitive *St. thermophilus* bacterium decreases the production of one or more pro-inflammatory cytokines in said subject.

42. The method of embodiment 41, wherein said pro-inflammatory cytokine is selected from the group consisting of: MIP1a, MIP3a, IL-16, IL-22, VEGF, eotaxin, IL-1b, KC, and LIF, or any combination thereof.

43. The method of any one of embodiments 37-42, wherein said therapeutically effective amount of the bacterium is about $10^8$ to $10^{12}$ CFU/day.

The following examples are offered by way of illustration and not by way of limitation.

EXPERIMENTAL

Example 1

Plasmids pUC57-AGRP-FH0, pUC57-AGRP-FH1 and pUC57-AGRP-FH2 containing the Gln-rich oligopeptides AGRP-FH0, AGRP-FH1 and AGRP-FH2 were constructed by GenScript Corporation (Piscataway, N.J.) based upon the amino acid sequences of the Gln-rich passenger domains shown below (Table 1). Each of the three oligopeptides contains a FLAG-tag epitope (DYKDDDDK, SEQ ID NO: 13). The Table also contains information of the molecular mass and isoelectric point of the encoded Gln-rich oligopeptide. The coding regions of the passenger were used in the construction of the St. thermophilus expression vectors described below.

The Gln rich oligopeptides contained in plasmids pUC57-AGRP-FH0, pUC57-AGRP-FH1 and pUC57-AGRP-FH2 can be designed to improve stability by taking into account length, Gln content, and the presence of protease cleavage sites that might promote their degradation upon release. Other amino acids could be included in the Gln rich peptides, such as arginine that have shown synergistic effects with Gln in oral rehydration therapy.

TABLE 1

First-generation AQ/AQR rich peptides for use in probiotics

| SEQ ID NO: | Construct | Passenger domain |
|---|---|---|
| 2 | AGRP-FH0 | RAMDYKDDDDKALQQAQQAQQKVQQDIQQPAQQAQQGQQQQAQQDIQQTAQQAQQIQQRQQKYPYDVPDYALD |
| 4 | AGRP-FH1 | RAMDYKDDDDKAQAQQGQRQAQQIQQAQQGQRQQAQAQQ QRQAQQIQQAQQGQRQQAQAQQGQQAQQIQQAQQGQRQQYPYDVPDYALD |
| 6 | AGRP-FH2 | RAMDYKDDDDKAQAQQRGQAQQRGQIQQRGQRAQAQQRGAQQRGQIQQRGQRAQAQQRGAQQRGQIQQRGQRAQAQQGQAQQRGQIQQRGQRYPYDVPDYALD |

FLAG-tag epitope underlined.

Example 2

Figure 2:
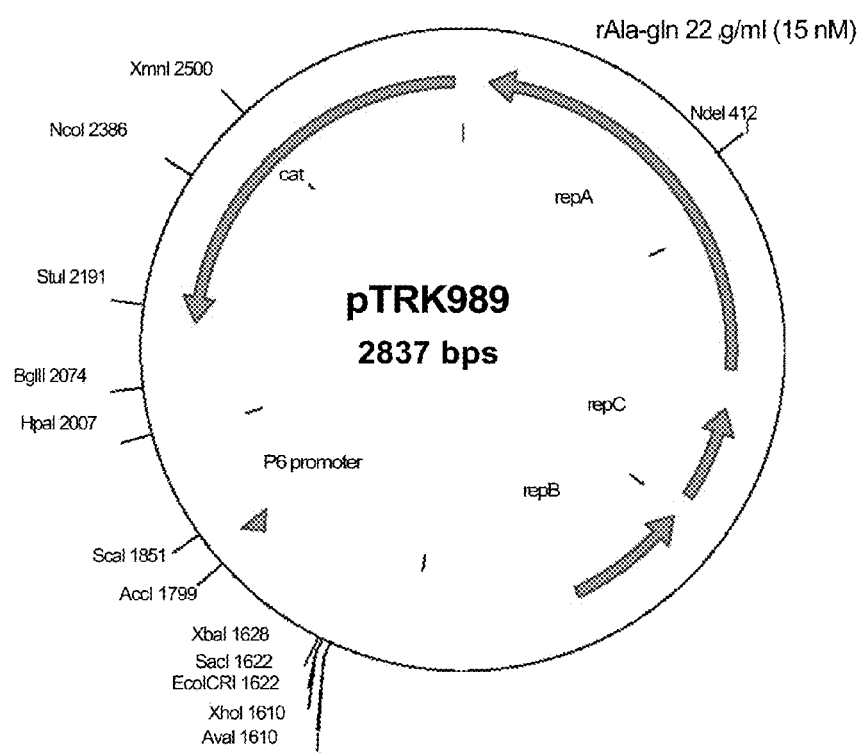
FIG. 2 illustrates a base vector (pTRK989) used for expressing AQ/AQR rich peptides in *St. thermophilus*.

St. thermophilus strain LMD-9 (also designated NCK1125) has a complete genome sequence (Makarova, 2006, Proc. Natl. Acad. Sci. USA, 103:15611-15616) and is genetically assessable by electroporation. This strain has been successfully used for cloning to a high copy vector (pTRK686) for elevated expression of antisense RNAs that were capable of retarding bacteriophage infection. In addition, the same base vector was used to express intracellularly, in trans, a phage primase that had been poisoned by a directed mutation. The vectors used to express the Gln-rich oligopeptide constructs were derived from pTRK686 and contain a multiple cloning site and a strong constitutive promoter that can be used to drive expression of the Gln-rich oligopeptide (See FIGS. 2 and 3).

The E. coli-gram positive shuttle vector pTRK989 was chosen for expression of the AQQ passenger sequences. Plasmid pTRK989 carries a strong P6 promoter, and is an XbaI-deleted derivative of pTRK696 used previously (Sturino, 2004, Appl Env Microbiol 70: 1735-1743). Nucleotide sequences encoding the AQ rich peptides were cloned in pTRK989 and resulting plasmids were transformed into E. coli MC1061 using the Z-Competent E. coli Transformation Buffer Set (Zymo Research). Transformants were recovered on LB plates with 20 ug/ml chloramphenicol. Isolates which had plasmids with the correct insert size were analyzed for insert orientation using Choice-Taq Blue DNA Polymerase (Denville Scientific Inc., Metuchen, N.J.) with a vector specific primer (Saul Forward: 5' TGCTGAAGAGCATCT-GATTG 3' (SEQ ID NO: 14) and an internal primer specific for each insert (FH0 int: 5' GGCCATGGATTATAAAGAC-GAC 3'(SEQ ID NO: 15); FH1 int: 5' GGGTCAACGTCAG-GCACAACAG 3'(SEQ ID NO: 16); FH2 int: 5' GATAAAGCCCAGGCCCAGCAAC 3'(SEQ ID NO: 17)).

Figure 3:
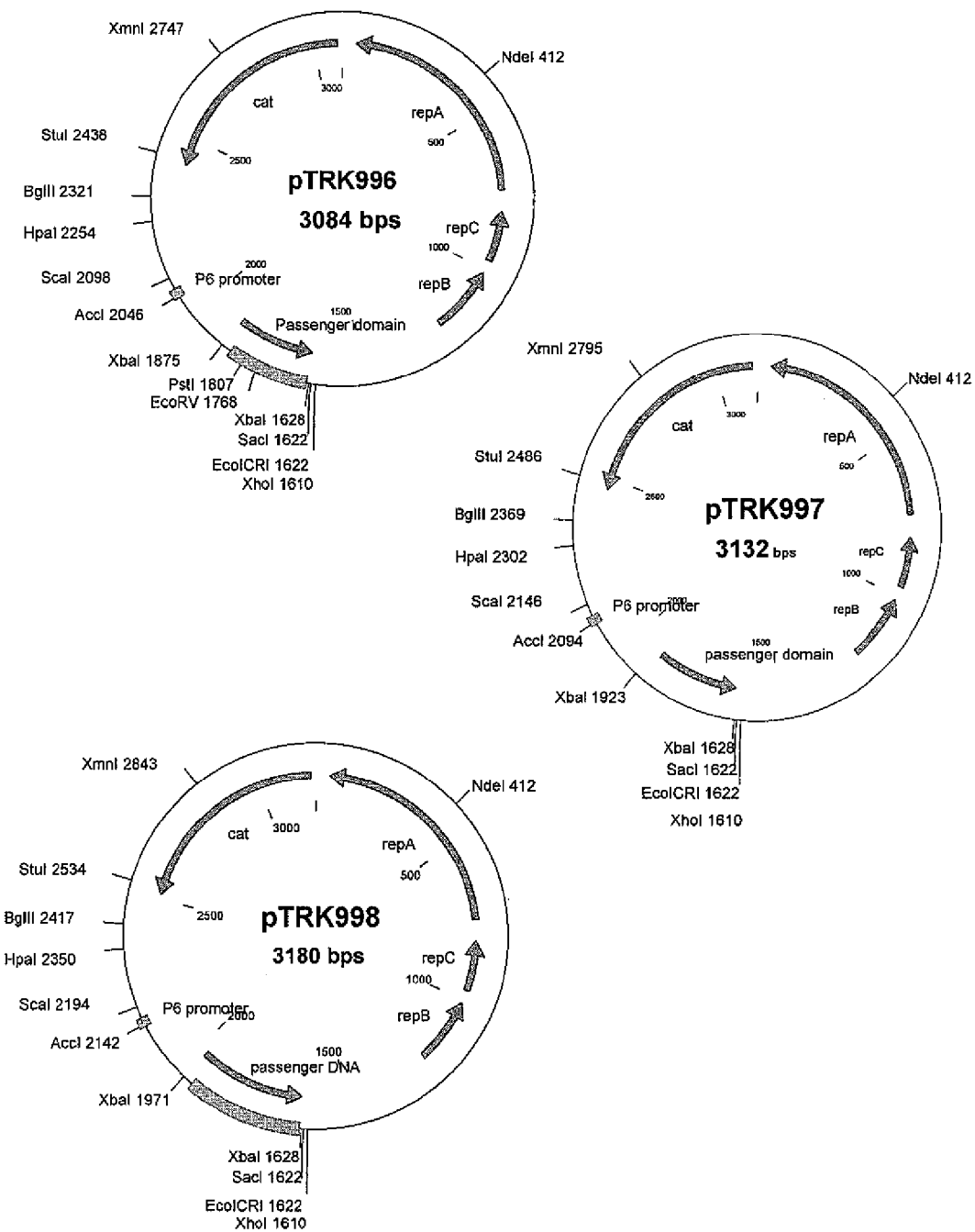
FIG. 3 illustrates the vectors used for expressing AQ/AQR rich peptides in *St. thermophilus*. pTRK996 encodes AGRP-FH0, pTRK997 encodes AGRP-FH1, and pTRK998 encodes AGRP-FH2.

One plasmid isolate of each construct with the proper orientation was sent to Davis Sequencing (Davis, Calif.) for sequencing of both strands of the insertions from flanking vector primers (Saul Forward, shown above, and Saul Reverse (5' CCCGTTAGTTGAAGAAGGTT 3' (SEQ ID NO: 18)). Maps of the plasmids are shown in FIG. 3. After confirmation of the sequences, the plasmids were transformed into St. thermophilus LMD-9 by electroporation (Sturino, 2004, Appl Env Microbiol 70: 1735-1743). Elliker-B plates with 5 ug/ml chloramphenicol were incubated anaerobically. Plasmid DNA from the isolates was amplified with the Saul Forward and Reverse primers (shown above), and the PCR products sequenced to confirm the sequence of the P6 promoter and polynucleotide encoding the AQ rich peptide in each construct.

Peptide expression was subsequently examined by Western blot using standard protocols. Both cell fractions and bile-treated cell supernatants were examined for the presence of AGRP-FH0, AGRP-FH1 and AGRP-FH2 oligopeptides.

Figure 4:
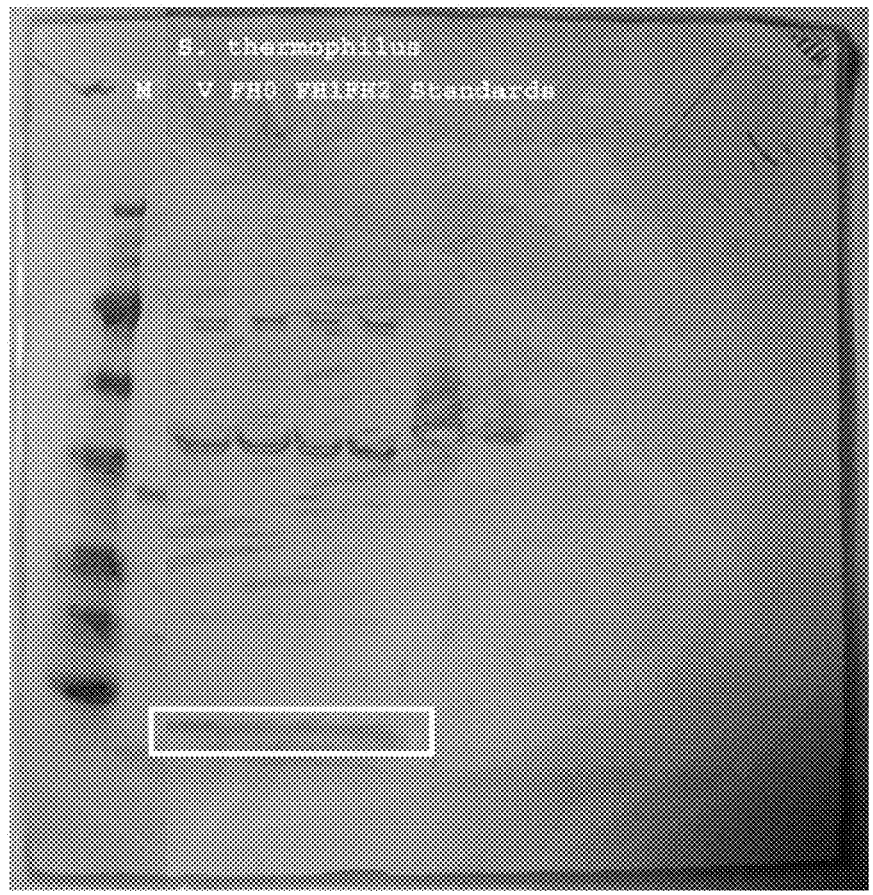
FIG. 4 shows the FLAG-BAP Western blot for AQ rich peptides AGRP-FH0, AGRP-FH1, and AGRP-FH2. Expression of each peptide can be seen in the area contained within the white box.

Briefly, St. thermophilus strains containing pTRK989 (control), pTRK996, pTRK997, and pTRK998, were grown to logarithmic phase ($OD_{600}$ ~0.6) in Belliker broth with appropriate antibiotic. Subsequently, 10 mL of logarithmic phase cultures were centrifuged and cell pellets were collected. Pellets were resuspended in 500 μL of PBS, subjected to BeadBeating for 2 min., and further centrifuged. Supernatants were collected and used for protein quantification and Western blotting. See FIG. 4.

| ATCC Deposit | Strain Designation | Plasmid constructs |
|---|---|---|
| | NCK1125 | St. thermophilus LMD-9, no vector |
| | NCK2070 | Contains pTRK989, used as a vector control |
| | NCK2071 | Contains pTRK996, encoding AGRP-FH0 (SEQ ID NO: 2) |
| | NCK2072 | Contains pTRK997, encoding AGRP-FH1 (SEQ ID NO: 4) |
| | NCK2073 | Contains pTRK998, encoding AGRP-FH2 (SEQ ID NO: 6) |

Example 3

Streptococcus thermophilus (LMD-9) was grown in Elliker's broth supplemented with 1% beef extract at 42° C. for 18 h resulting in $10^9$ CFU/mL. Cultures for use as an in vivo treatment were pelleted, washed, and resuspended in broth to a final concentration of 10⁸/mL. A clinical BI strain of *Clostridium difficile* (UVA24; TcdA⁺, TcdB⁺, CdtA/B⁺) or the historical strain, VPI10463 was used in the studies outlined below. *C. difficile* were grown in pre-reduced chopped meat broth for 18 h at 37 C for use in vivo or overnight in BHI broth for in vitro studies. *C. difficile* was enumerated on BHI agar containing 0.5% neutral red (1% w/v in ethanol) using the broth microdilution and the drop plate method (Chen, 2003, *J. Microbiol. Methods*, 55(2): 475-479).

Example 4

A mouse model of *C. difficile*-associated disease (Chen, 2008, *Gastroenterology*, 135(6): 1984-1992) was used for in vivo studies with the following modifications: omission of kanamycin from the antibiotic cocktail and an increase in clindamicin (32 mg/kg). All experiments were conducted according to the protocol approved by the University of Virginia ACUC. Male mice (8 w.o., Jackson Laboratories) were used in all studies. *St. thermophilus* treatment ($10^7$ CFU/100µL) was administered within 72 h of the antibiotic cocktail and every 24 h thereafter by oral gavage. Animals were infected with the clinical isolate, UVA24 ($10^5$ CFU/100 uL). *St. thermophilus* treatment was discontinued if diarrhea was evident. Animals were observed and weighed at the same time, daily. The severity of diarrhea was scored using the following scale: 0—no symptoms, 1—clumped cobb, 2—slight wet tail, and 3—wet tail. On days three and five, mice with similar clinical signs were euthanized for sample collection (cecal contents and tissue). Samples were either frozen and stored at ⁻80° C. or fixed in Bouin's solution; paraffin embedded, and stained using hematoxylin/eosin (services provided by the University of Virginia Research Histology Core). Slides were blinded and scored by an independent reader using published parameters (Pawlowski, 2010, *J Infect Dis* 202(11): 1708-1712).

Example 5

All assays were performed in a Bactron I anaerobic chamber (Shel Labs, Cornelius, Oreg.). *C. difficile* ($10^5$ CFU) was inoculated into broth containing supernatants, L-lactic acid, or HEPES buffer (50 mM). Supernatants from *St. thermophilus* were filtered (0.2 µm) and diluted to 50% (v/v) with BHI to support growth of *C. difficile*. Similarly, stocks of L-lactic acid were diluted in BHI to a final concentration of 10-100 mM. After inoculation and growth (24 h, 37° C.), bacteria were enumerated on BHI agar as described above.

Example 6

A commercially available kit (*C. difficile* Toxin A/B II, Techlab, Blacksburg, Va.) was used for detection of toxin(s) in the cecal contents of mice or from in vitro supernatants. Cecal contents were weighed and normalized to the sample weighing the least using the sample diluent provided in the kit. Normalized samples were diluted 1:1000, and 150 uL tested according to the manufacturer's directions. In vitro supernatants were tested at 1:10 dilution using the kit.

Example 7

In order to understand the impact of *St. thermophilus* on antibiotic associated *C. difficile* infection, viable *St. thermophilus* was administered to mice daily at a dose similar to that used in humans (e.g., $5 \times 10^{10}$ CFU per 70 kg human, (McFarland, 2009, *Anaerobe*, 15(6): 274-280)) within the first 72 h of starting the antibiotic cocktail and was continued daily throughout the course of infection. Initial studies used VPI10463 at $10^4$ CFU ($LD_{50}$), although only 30% died with *St. thermophilus* treatment (vs. 50% of control; data not shown), this trend was not significant and the subsequent focus of our studies was on a clinical isolate.

Figure 1:
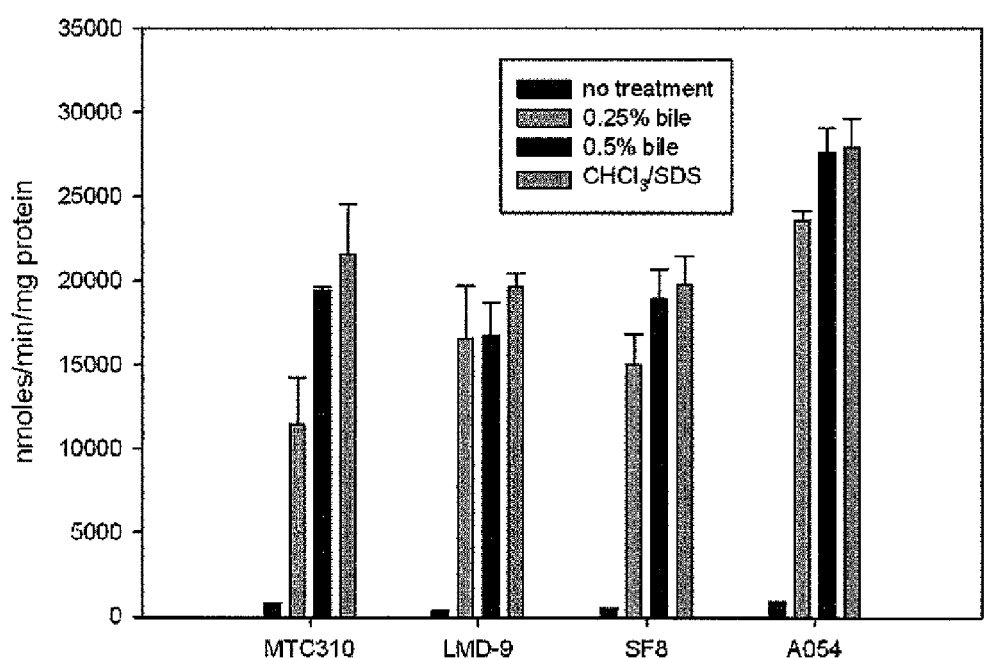
FIG. 1 shows the permeabilization of selected strains of *St. thermophilus* following bile exposure by quantification of extracellular beta-galactosidase activity.

A toxigenic clinical REA type BI isolate (i.e., UVA24) from a patient with *C. difficile* colitis was used to infect mice and provide sufficient morbidity with little mortality. Using this strain, mice receiving *St. thermophilus* lost significantly less weight (46%) due to *C. difficile* infection than controls (FIG. 1A). During infection, mice were scored daily for signs of diarrhea where data from days three and four post-infection (FIG. 1D) show a reduction in diarrheal incidence in *St. thermophilus* treated mice. In a separate experiment, UV-irradiated, nonviable *St. thermophilus* was given to mice and showed no differences in weight or diarrhea compared to the infected controls. On day three post-infection, cecal contents and tissue samples were taken from treated and untreated mice and analyzed for levels of TcdA/B and histopathology, respectively (FIG. 4B,C). Toxin levels in the cecal contents provide a measure of not only release of TcdA/B by *C. difficile*, but can also serve as an indicator of disease progression in mice where lower levels are seen later in infection (i.e., day five versus three). Although TcdA/B levels were not significantly different, mice treated with *St. thermophilus* tended to have lower detectable levels of toxins. Similarly, *St. thermophilus* treated mice had a lower severity of diarrhea (FIG. 4D). Histopathology scoring showed that mice treated with *St. thermophilus* had significantly less *C. difficile*-associated pathology in the colon and less cecal pathology (FIG. 4C).

Interestingly, comparable levels of *C. difficile* were detected in the cecal contents using real-time PCR targeted at tcdB (average $C_T$ values on day 3 were 34.67 and 34.49 for untreated and treated, respectively; n=8 wells/group). In total, in vivo results suggested an impact of *St. thermophilus* on the toxin production by *C. difficile*; therefore, additional in vitro experiments were done to elucidate the mode of action.

Example 8

Filtered supernatants (50% v/v) from *St. thermophilus* were tested for activity on *C. difficile* and showed a 5-log reduction after 24 h (FIG. 5A). The activity was dose dependant since less supernatant (33% v/v) was permissive of *C. difficile* growth after 24 h (data not shown). The major constituents secreted by several lactic acid bacteria include lactic acid, hydrogen peroxide, and bacteriocins. The experiments presented here were designed to characterize the effect of one of these components, lactic acid, on *C. difficile*. To test the involvement of lactic acid produced by *St. thermophilus*, filtered supernatants (50% v/v) were buffered, inoculated with *C. difficile*, and growth quantified after 24 h. In this experiment, the buffer changed the pH of the media from 5 to 5.8 and permitted *C. difficile* survival at the initial levels inoculated suggestive of a bacteriostatic effect (FIG. 5A). Further experiments using L-lactic acid show high doses (100 mM) are bactericidal to *C. difficile* despite buffer while 10-fold lower levels permit growth and buffering the media appears to allow additional growth (FIG. 5B). Similar effects of L-lactic acid (1 and 10 mM) were observed with VPI10463 while 100 mM completely ablated growth after 24 h (data not shown).

The final aspects of defining the effects of lactic acid on *C. difficile* in this study involved examining the relative abundance of TcdA during growth to corroborate in vivo findings of lower toxin levels in animals treated with *St. thermophilus*.

C. difficile supernatants (i.e., 24 h growth in the presence of lactic acid±buffer) were tested for toxins using the TcdA/B ELISA and show that although 10 mM lactic acid permits bacterial growth (FIG. 5B); toxin production is dose-dependently decreased in the absence of buffer (FIG. 5C).

Example 9

C. difficile is a ubiquitous bacterial species comprised of primarily toxigenic and nontoxigenic strains associated with humans and animals. The study presented here sought to examine the impact of St. thermophilus on experimental C. difficile infection with a BI strain. Similar to previous studies (Chen, 2008, Gastroenterology, 135(6): 1984-1992), infections with a BI strain resulted in lower mortality rates in vivo compared to VPI10463. Animals treated with viable St. thermophilus lost significantly less weight indicative of lower diarrheal severity, showed less pathology and lower cecal toxin levels compared to untreated controls; however, the burden of C. difficile in the cecal contents by PCR was independent of treatment. One limitation with PCR is that the viability of the organism is not taken into account.

Nevertheless, our findings are reflective of studies that examined the impact of colonization and cytotoxicity in gnotobiotic mice with human isolates prior to C. difficile challenge (Corthier, 1985, Appl Environ microbial 49(1): 250-252). The authors found that C. difficile-infected mice monoassociated with Bifidobacterium bifidum or Escherichia coli had low cecal levels of cytotoxin (i.e., TcdB) despite high levels of pathogen. Although the data presented in this work did not specifically look at TcdB, both studies suggest a role for specific bacteria and/or bacterial metabolites that suppress C. difficile toxin production.

The results presented here build on a working model of C. difficile infection for testing clinically relevant treatments that may be used to guide probiotic usage among patients with C. difficile. At a more basic level, the model permits examination of the intestinal microbiome after antibiotic exposure and/or use of probiotic organisms on disease susceptibility. It is possible that both inter- and intra-bacterial metabolic processes are crucial to suppressing C. difficile toxin metabolism and therefore disease development.

Example 10

Cell migration assay was used to measure levels of mucosal damage. This assay was performed as previously described (McCormack, 1992, Am J Physiol 263: G426-G435). For this assay 35-mm dishes were coated with Matrigel according to the manufacturer's instructions (40µg/ml). To initiate migration, IEC-6 cells were plated at $6.25 \times 10^4$ cells/cm2 and grown to confluence. After 6 days, we scraped the cell layer with a razor blade, beginning at the diameter of the dish and extending over a 30-mm-wide area. After scraping, the medium was changed to normal medium and 1, 10, or 100 ng/ml toxin A was added. In the following experiments, the replacement of medium was made with Gln-free medium or medium with Gln or Ala-Gln (10 mM), and then toxin A (10 ng/ml) was added. In order to verify the effect of Gln and Ala-Gln on the migration after mechanical damage, the replacement of medium after scraping was made with medium without Gln or medium with Gln or Ala-Gln (1, 3, 10, or 30 mM) in the absence of toxin A. The dishes were then returned to the incubator, and after 6 and 24 hr the area with the highest migration rate was photographed. The cells were counted using an eyepiece grid.

Example 11

Dose Response and Time Course of the Toxin A-Induced Apoptosis by AnnexinV Assay. IEC-6 cells were seeded in sixwell plates (106 cells/well), and 24 hr after plating, the medium was changed to normal medium or medium containing Gln or Ala-Gln (10 mM), and the cells were incubated with or without toxin A (1-1000 ng/ml). After 24 hr for dose response and 2, 6, 18, and 24 hr of incubation with toxin A for time course, the medium was discharged, and the attached cells were washed with PBS, trypsinized, collected by centrifugation, and double stained with fluorescein isothiocyanate-conjugated Annexin V and propidium iodide (ApoAlert Annexin V Apoptosis Kit; Clonetech, Palo Alto, Calif.). The percentage of apoptotic and necrotic cells was measured by flow cytometry.

That which is claimed:

1. A *Streptococcus thermophilus* bacterium that is genetically modified to express a heterologous polypeptide comprising an amino acid sequence having at least 90% sequence identity to the amino acid sequence as set forth in SEQ ID NO: 2 or 8, wherein said heterologous polypeptide is released from said bacterium following exposure to bile.

2. The bacterium of claim 1, wherein said heterologous polypeptide is a therapeutic polypeptide.

3. The bacterium of claim 1, wherein said heterologous peptide comprises
an amino acid sequence selected from the group consisting of: SEQ ID NO: 2 and 8.

4. The bacterium of claim 1, wherein said bacterium does not survive said bile exposure.

5. The bacterium of claim 1, wherein said *Streptococcus thermophilus* is selected from the group consisting of:

a) *Streptococcus thermophilus* NCK2071, having been deposited under ATCC Accession Number PTA-11889; and
b) a probiotic *Streptococcus thermophilus* bacterium.

6. A method of making a *Streptococcus thermophilus* bacterium, said method comprising genetically modifying said bacterium to express a heterologous polypeptide comprising an amino acid sequence having at least 90% sequence identity to the amino acid sequence as set forth in SEQ ID NO: 2 or 8, wherein said polypeptide is released from said bacterium following exposure to bile.

7. The method of claim 6, wherein said heterologous polypeptide comprises an amino acid sequence selected from the group consisting of:
SEQ ID NO: 2 and 8.

8. A pharmaceutical composition comprising the bacterium according to claim 1.

* * * * *